(12) United States Patent
Bonvallet et al.

(10) Patent No.: US 8,523,874 B2
(45) Date of Patent: Sep. 3, 2013

(54) INSTRUMENTS AND TECHNIQUES FOR SEPARATING BONY STRUCTURES

(75) Inventors: Todd C. Bonvallet, Hixson, TN (US); Eric C. Lange, Germantown, TN (US); Tom J. Francis, Cordova, TN (US); Steven D. DeRidder, Bartlett, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 552 days.

(21) Appl. No.: 12/802,425

(22) Filed: Jun. 7, 2010

(65) Prior Publication Data

US 2010/0249792 A1  Sep. 30, 2010

Related U.S. Application Data

(63) Continuation of application No. 10/441,689, filed on May 20, 2003, now Pat. No. 7,749,231.

(60) Provisional application No. 60/382,408, filed on May 21, 2002, provisional application No. 60/411,562, filed on Sep. 18, 2002.

(51) Int. Cl.
*A61B 17/56* (2006.01)
*A61B 17/88* (2006.01)

(52) U.S. Cl.
USPC .................................................. 606/99

(58) Field of Classification Search
USPC ............. 606/246, 57, 79, 82, 84, 279, 205, 606/99, 90, 105, 86 A
See application file for complete search history.

(56) References Cited

U.S. PATENT DOCUMENTS

| | | |
|---|---|---|
| 1,557,370 A | 10/1925 | Lane |
| 4,271,836 A | 6/1981 | Bacal et al. |
| 4,501,266 A | 2/1985 | McDaniel |
| 4,896,661 A | 1/1990 | Bogert et al. |
| 4,898,161 A | 2/1990 | Grundei |
| 4,997,432 A | 3/1991 | Keller |
| 5,019,081 A | 5/1991 | Watanabe |
| 5,122,130 A | 6/1992 | Keller |
| 5,213,112 A | 5/1993 | Niwa et al. |
| 5,297,538 A | 3/1994 | Daniel |
| 5,314,477 A | 5/1994 | Marnay |
| 5,431,658 A | 7/1995 | Moskovich |
| 5,529,571 A | 6/1996 | Daniel |
| 5,540,696 A | 7/1996 | Booth, Jr. et al. |
| 5,571,109 A | 11/1996 | Bertagnoli |
| 5,649,929 A | 7/1997 | Callaway |
| 5,746,768 A | 5/1998 | Lewis et al. |
| 5,769,782 A | 6/1998 | Phan |
| 5,888,227 A | 3/1999 | Cottle |

(Continued)

FOREIGN PATENT DOCUMENTS

| | | |
|---|---|---|
| EP | 1222903 | 10/2001 |
| WO | WO 02/069811 | 9/2002 |

OTHER PUBLICATIONS

Surgical Technique Using FRA Spacer Instruments—Technique Guide; Synthes Spine; 1998.

(Continued)

*Primary Examiner* — Pedro Philogene
*Assistant Examiner* — David Comstock

(57) ABSTRACT

Instruments and techniques separate or spread adjacent bony structures by inserting a distal spreader assembly into the space between the adjacent bony structures and actuating the spreading members with a proximal actuator assembly.

20 Claims, 20 Drawing Sheets

(56) References Cited

U.S. PATENT DOCUMENTS

| | | |
|---|---|---|
| 5,899,901 A | 5/1999 | Middleton |
| 5,984,922 A | 11/1999 | McKay |
| 5,997,565 A | 12/1999 | Inoue |
| 6,017,342 A | 1/2000 | Rinner |
| 6,159,215 A | 12/2000 | Urbahns et al. |
| 6,261,296 B1 | 7/2001 | Aebi et al. |
| 6,478,800 B1 | 11/2002 | Fraser et al. |
| 6,551,316 B1 | 4/2003 | Rinner et al. |
| 6,569,168 B2 | 5/2003 | Lin |
| 6,652,533 B2 | 11/2003 | O'Neil |
| 6,716,218 B2 | 4/2004 | Holmes et al. |
| 7,081,118 B2 | 7/2006 | Weber et al. |
| 2002/0026191 A1 | 2/2002 | Dixon et al. |
| 2002/0165550 A1 | 11/2002 | Frey et al. |
| 2003/0225416 A1 | 12/2003 | Bonvallet et al. |
| 2004/0106927 A1 | 6/2004 | Ruffner et al. |

OTHER PUBLICATIONS

M. Aebi, J.S. Thalgott, J.K. Webb—AO ASIF Principles in Spine Surgery; 1998.

Compressors and Distractors Brochure; Beere Precision Medical Instruments; 1977.

Keystone Craft Instruments; Depuy Motech; 1998.

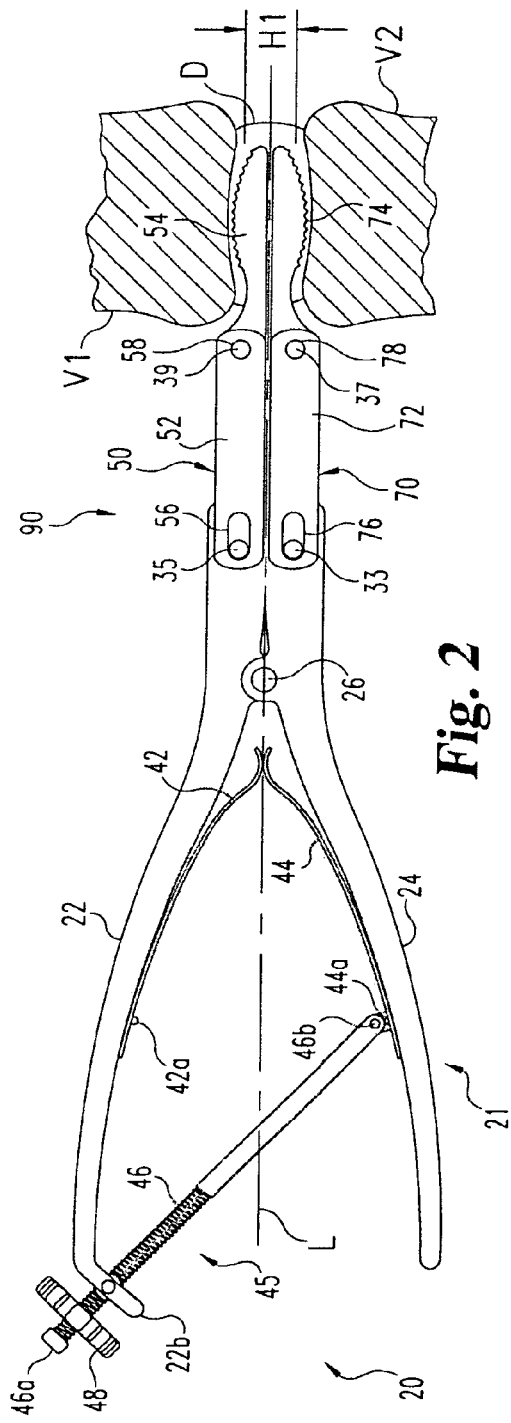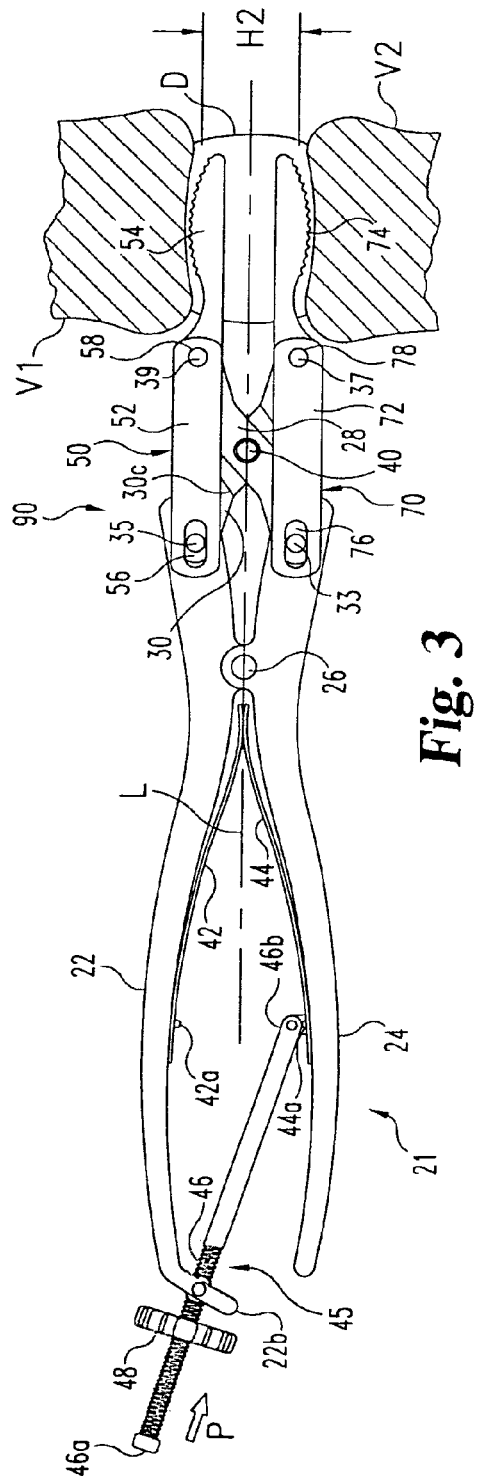

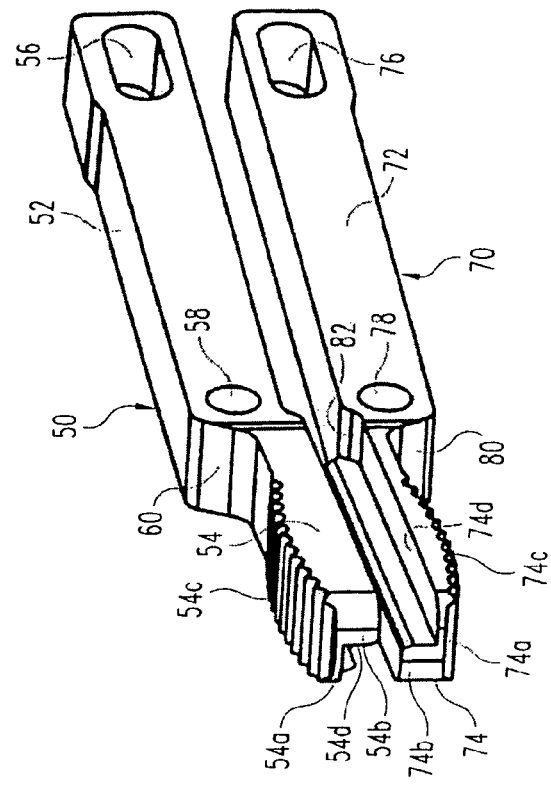
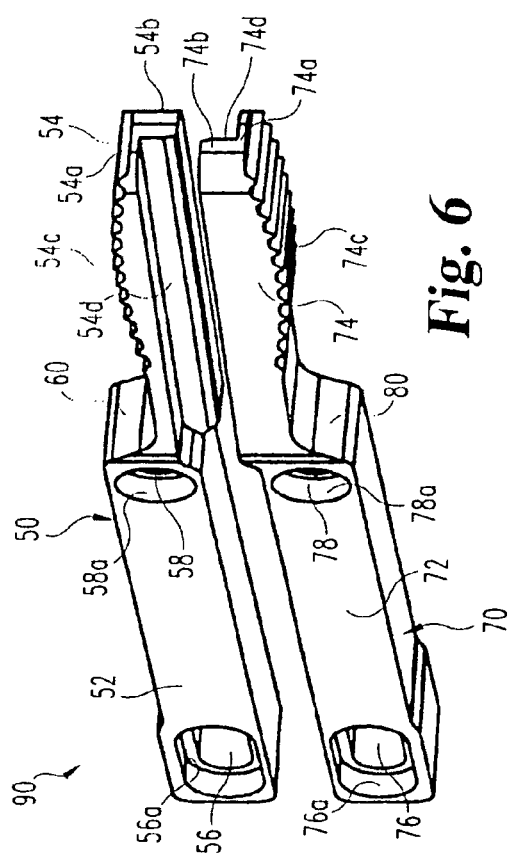
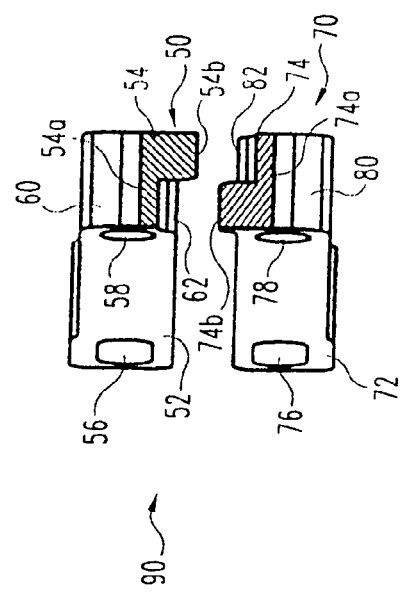

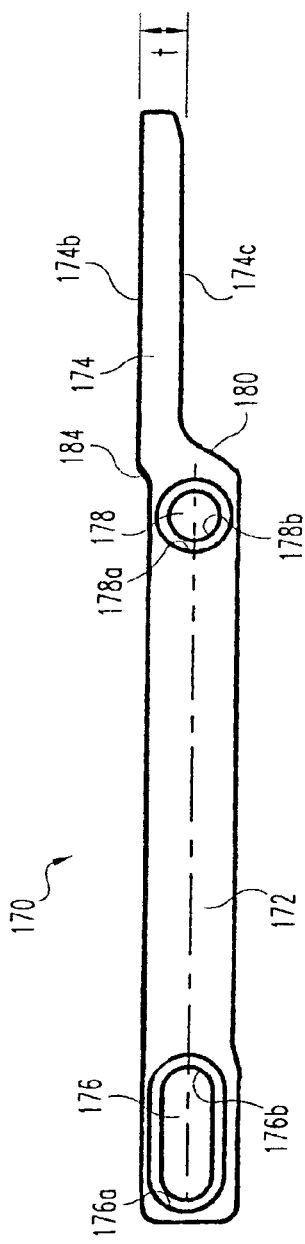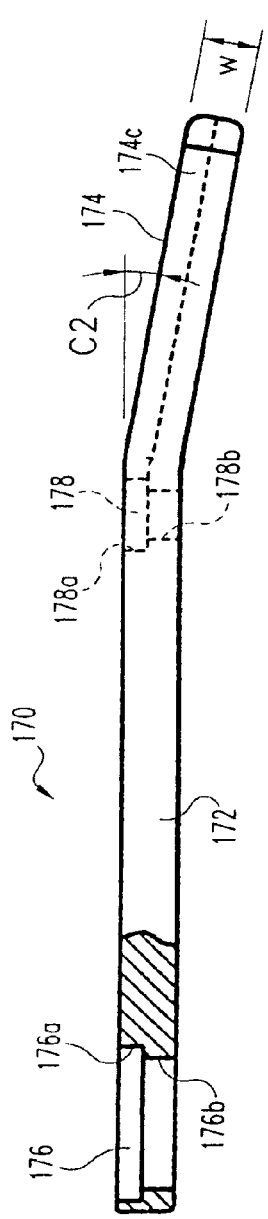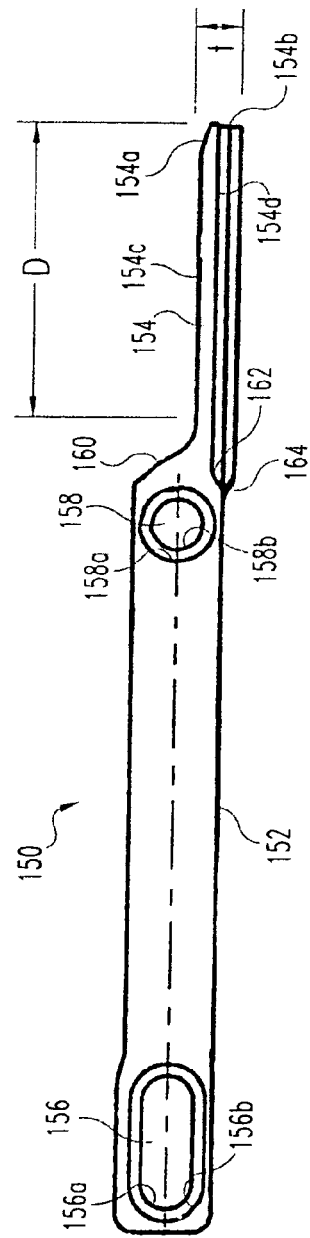

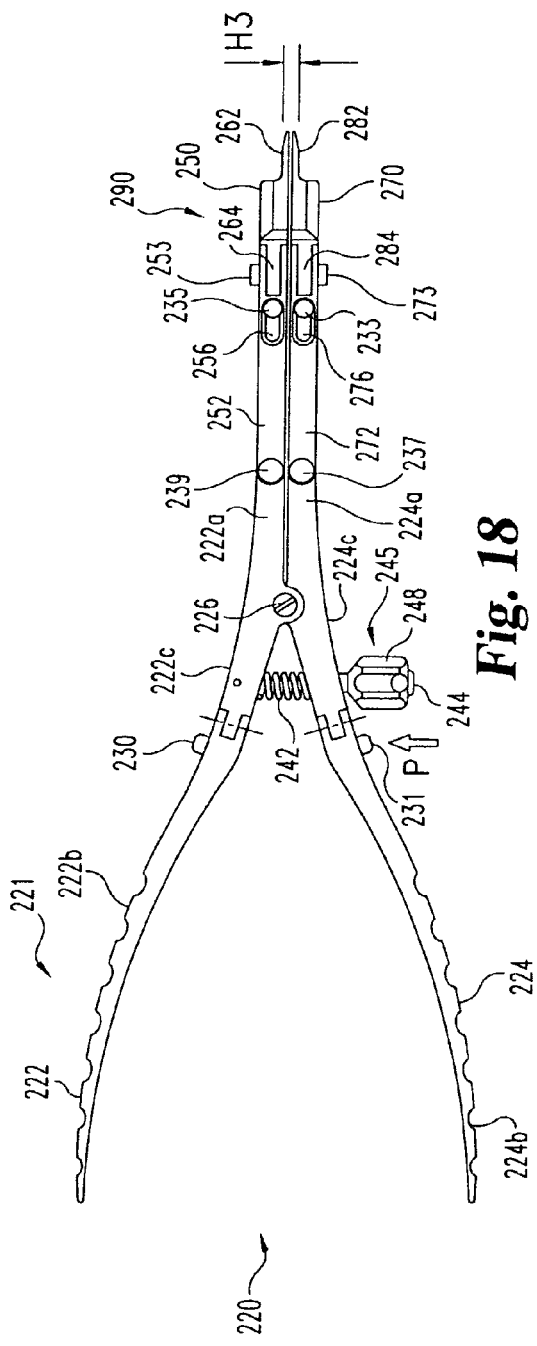
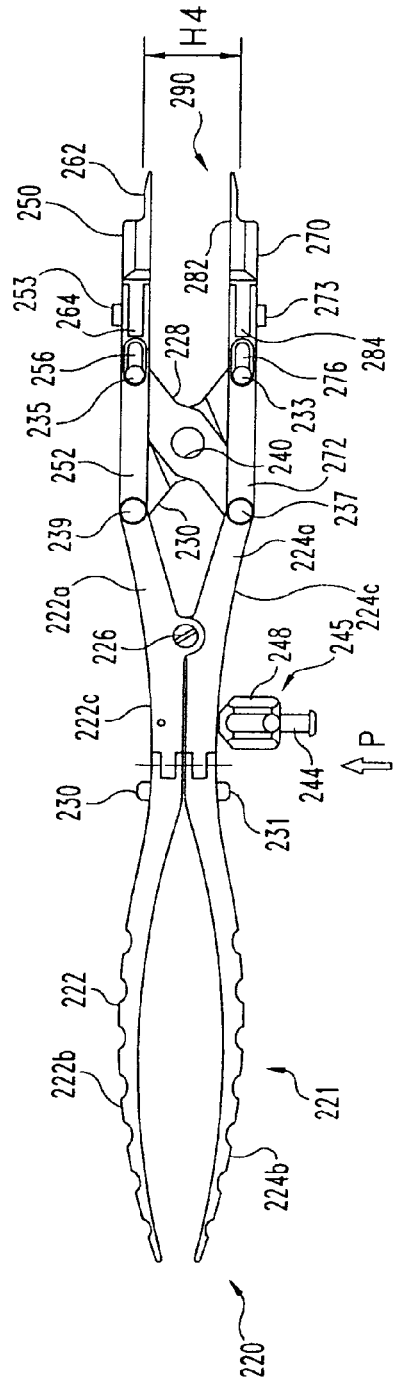
Fig. 18
Fig. 19

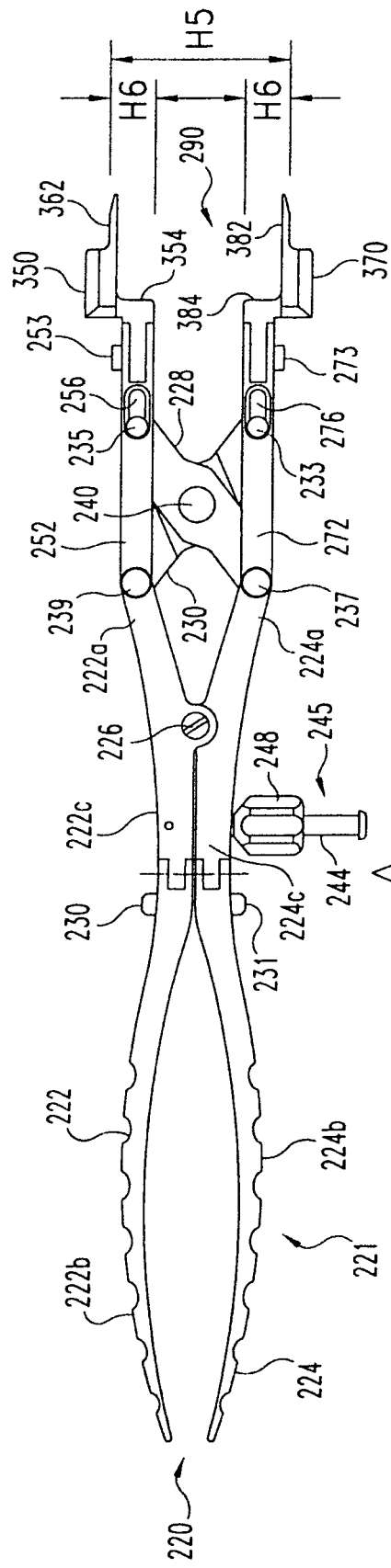
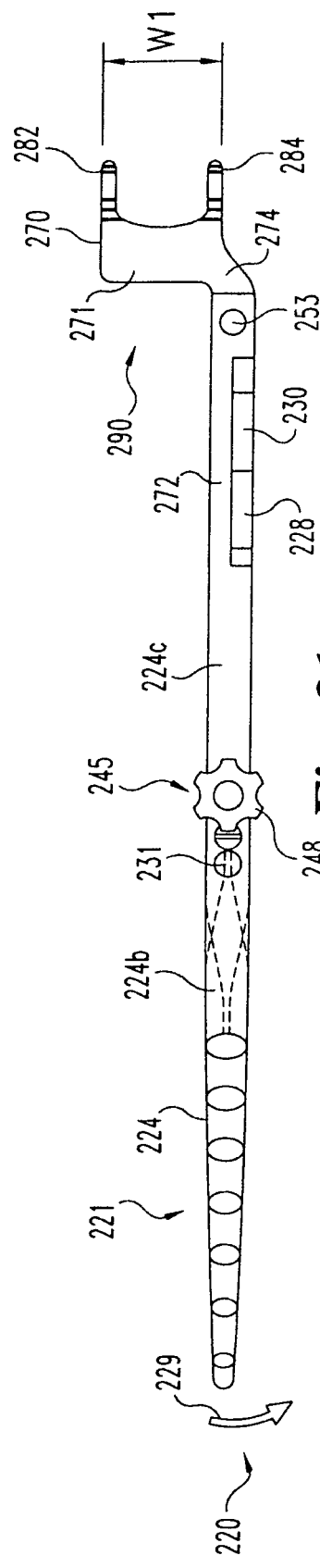
Fig. 20
Fig. 21

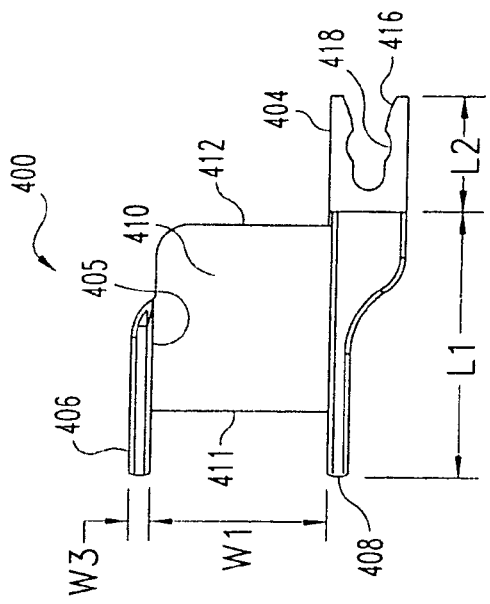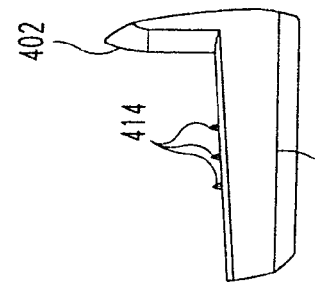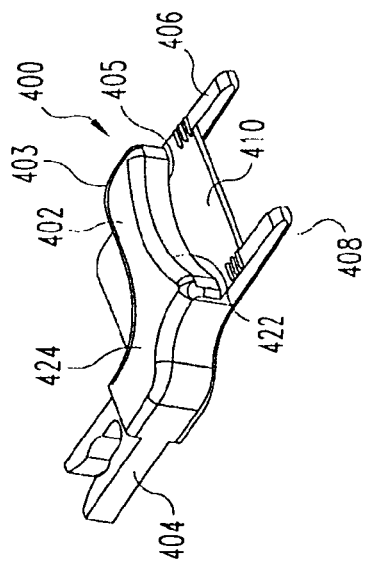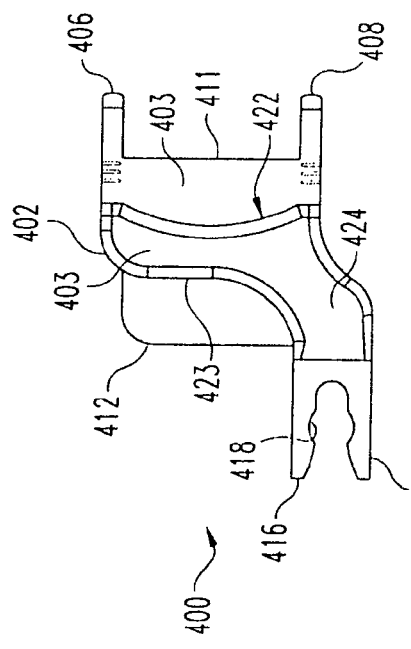

INSTRUMENTS AND TECHNIQUES FOR SEPARATING BONY STRUCTURES

CROSS-REFERENCE TO RELATED APPLICATIONS

This application is a continuation of U.S. patent application Ser. No. 10/441,689 filed May 20, 2003 now U.S. Pat. No. 7,749,231, which claims the benefit of the filing date of U.S. Provisional Application Ser. No. 60/382,408 filed on May 21, 2002 and also claims the benefit of the filing date of U.S. Provisional Application No. 60/411,562 filed on Sep. 18, 2002. The referenced applications are incorporated herein by reference in their entirety.

BACKGROUND

Adjacent bony structures can require separation for appropriate treatment or repositioning of the bony structures. Separating the bony structures can facilitate insertion of instruments and implants into the space between bony structures.

For example, the spinal disc space between adjacent vertebrae can collapse completely or partially, causing pain and trauma for the afflicted person. Other conditions associated with the spinal column can also require access to a spinal disc space for appropriate treatment. Surgical techniques for treating such conditions can require the adjacent vertebrae to be distracted or spread apart to restore or partially restore the spacing, or to increase the spacing, between the adjacent vertebrae.

There remain various needs for instruments and techniques that can be employed for separating bony structures. The present invention is directed to meeting these needs, among others.

SUMMARY

The invention relates to instruments and techniques for separating adjacent bony structures.

According to one aspect, a spreader instrument is provided that includes a distal spreader assembly for insertion in the space between bony structures and a proximal actuator assembly for actuating the spreader assembly to separate the bony structures.

According to another aspect, a spreader instrument is provided that includes a distal spreader assembly for insertion in the space between bony structures and a proximal actuator assembly for actuating the spreader assembly to separate the bony structures. The distal spreader assembly includes opposite bony structure contacting surfaces, at least one of which includes an etched bone contacting surface.

According to a further aspect, a spreader instrument is provided that includes a distal spreader assembly for insertion in the space between bony structures and a proximal actuator assembly for actuating the spreader assembly to separate the bony structures. The spreader assembly includes opposite surfaces for contacting bony structures. The opposite surfaces each include bone engaging features for engaging the adjacent bony structure to maintain the spreader assembly in contact therewith. Bone engaging features may include any one or combination of pitting, knurling, serrations, teeth, ridges, barbs, spikes, peeks and valleys, grooves, concave curvature, and convex curvature.

According to another aspect, a spreader instrument is provided that includes a distal spreader assembly for insertion in the space between bony structures and a proximal actuator assembly for actuating the spreader assembly to separate the bony structures. The spreader assembly includes first and second spreading members that are positionable adjacent one another in a low profile configuration for insertion into the space between the bony structures and thereafter movable away from one another to contact respective ones of the adjacent bony structures to separate the bony structures. The low profile arrangement can include, for example, nesting the spreading members, collapsing of the spreading members, overlapping the spreading members, and/or compressing the spreading members.

According to a further aspect, a spreader instrument is provided that includes a distal spreader assembly for insertion in the space between bony structures and a proximal actuator assembly for actuating the spreader assembly to separate the bony structures. The spreader assembly includes spreading members having opposite surfaces for contacting the bony structure. The spreading members are engaged to the actuator assembly so that the spreading members remain parallel to one another as the spreading members are moved away from one another to spread the adjacent bony structure. The engagement of each of the spreading members to the actuator assembly can include a fastener movably received in a slot so that a connection location between the actuator assembly and the respective spreading member is variable within the slot.

According to a further aspect, a spreader instrument is provided that includes a distal spreader assembly for insertion in the space between bony structures and a proximal actuator assembly for actuating the spreader assembly to separate the bony structures. The spreader assembly includes opposite spreading members for contacting the bony structure. The spreading members each have a length sufficient to extend in the space across a substantial portion of the adjacent bony structures. The spreading members each have a cross-sectional modulus or moment of inertia that limits deflection of the spreading member within an acceptable range when the spreading member applies a separating force to the adjacent bony structure.

In another aspect of the invention, a spreader instrument is provided with spreading members for contacting bony structures. The cross-sections of the spreading members provide a low profile configuration when the spreading members are positioned adjacent one another for insertion of the spreading members into the space between the adjacent bony structures. The length to depth ratio of the spreading members can also be sufficient to provide adequate resistance to bending of the spreading members.

According to another aspect, a method for separating adjacent vertebrae is provided. Spreading members are inserted into an at least partially collapsed disc space between the adjacent vertebrae. The spreading members are actuated to spread the adjacent vertebrae. The spreading members have a length sufficient to spread or distract the entire depth of the disc space between the vertebrae. Instruments are inserted into the disc space to perform surgical procedures while the spreading members maintain separation of the vertebrae. One or more implants can also be inserted in the disc space while the spreading members maintain separation of the adjacent vertebrae.

According to one aspect, a spreader instrument is provided that includes a distal spreader assembly for insertion in the space between bony structures and a proximal actuator assembly for actuating the spreader assembly to separate the bony structures. The distal spreader assembly includes a pair of spreading members each having at least one support surface extending therealong adapted to guide a cutting instrument in a spinal disc space.

According to a further aspect, a spreader instrument is provided that includes a distal spreader assembly for insertion in the space between bony structures and a proximal actuator assembly for actuating the spreader assembly to separate the bony structures. The distal spreader assembly includes a pair of spreading members each having a guide member. Disc space preparation, implants, and/or implant insertion instruments can be guided into the disc space between the guide members.

According to one aspect, a spreader instrument is provided that includes a distal spreader assembly for insertion in the space between bony structures and a proximal actuator assembly for actuating the spreader assembly to separate the bony structures. The distal spreader assembly includes a pair of spreading members each having a pair of distal extension members positionable in the spinal disc space. For each spreading member, one of the distal extension members is longer than the other distal extension member.

According to another aspect, a spreader instrument is provided that includes a distal spreader assembly for insertion in the space between bony structures and a proximal actuator assembly for actuating the spreader assembly to separate the bony structures. The distal spreader assembly includes a pair of spreading members each having a pair of distal extensions positionable in the spinal disc space. Each spreading member includes a stepped region to increase the spacing between the spreading members.

These and other aspects of the invention will be apparent from the following description of the illustrated embodiments.

BRIEF DESCRIPTION OF THE FIGURES

FIG. 2 is an elevation view of one embodiment of a spreader instrument having spreading members positioned in a space between adjacent bony structures in an unactuated state.

FIG. 3 is an elevation view of the spreader instrument of FIG. 2 in an actuated state.

FIG. 6 is a perspective view of a distal spreader assembly comprising a portion of the spreading instrument of FIG. 2.

FIG. 7 is another perspective view of the distal spreader assembly of FIG. 6.

FIG. 8 is a sectional view through the spreading members of the distal spreader assembly of FIG. 6.

FIG. 15 is an elevation view looking at the side of a second spreading member of the distal spreader assembly of FIG. 12.

FIG. 16 is an elevation view looking at the contact surface of the spreading member of FIG. 15.

FIG. 17 is an elevation view looking at the side of the first spreading member of the distal spreader assembly of FIG. 12.

FIG. 18 is an elevation view of another embodiment spreader instrument in an unactuated position.

FIG. 19 is an elevation view of the spreader instrument of FIG. 18 in an actuated position.

FIG. 20 is an elevation view of the spreader instrument of FIG. 18 in an actuated position and having an alternate distal end arrangement to provide greater spreading distance capability.

FIG. 21 is a plan view of the spreader instrument of FIG. 18.

FIG. 22 is a perspective view of one embodiment spreading member useable with, for example, the spreader instrument of FIG. 18.

FIG. 23 is a bottom plan view of the spreading member of FIG. 22.

FIG. 24 is a top plan view of the spreading member of FIG. 22.

FIG. 25 is a detail view of a portion of the spreading member of FIG. 22.

DESCRIPTION OF THE ILLUSTRATED EMBODIMENTS

Figure 1:
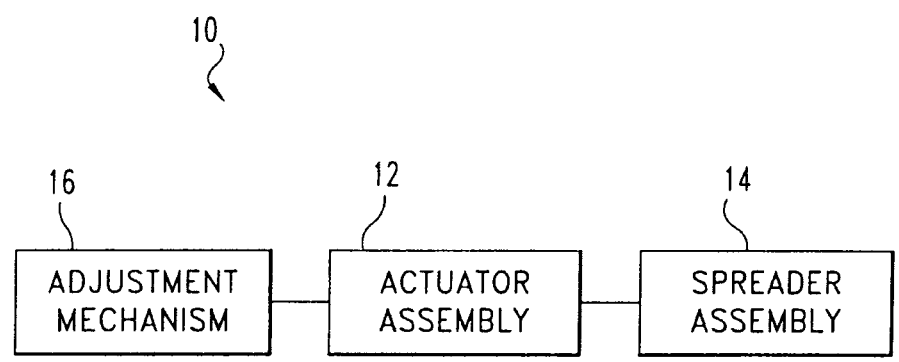
FIG. 1 is a diagrammatic illustration of a spreader instrument.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device and any such further applications of the principles of the invention as illustrated therein are contemplated as would normally occur to one skilled in the art to which the invention relates.

Referring to FIG. 1, a diagrammatic illustration of one embodiment of a spreader instrument 10 for insertion into the space between adjacent bony structures and for spreading the adjacent bony structures is shown. Spreading instrument 10 includes a proximal actuator assembly 12 and a distal spreader assembly 14. Actuator assembly 12 provides remote actuation of spreader assembly 14 when spreader assembly 14 is positioned within the space between adjacent bony structures. Actuator assembly 12 also releasably maintains spreader assembly 14 in the actuated position. Spreader instrument 10 can be used to access the space between adjacent bony structures in an open or minimally invasive procedure. Additionally, actuator assembly 12 can include an adjustment mechanism 16 to effect an adjustment of the actuated position of spreader assembly 14 achieved through actuator assembly 12.

Proximal actuator assembly 12 includes any device or mechanism capable of adjusting the position or orientation of distal spreader assembly 14. Actuator assembly 12 may include linkage systems, wire systems, gear systems, and flexible adjustment systems, for example. Actuator assembly 12 may include linear and/or rotationally moving elements. Actuator assembly 12 may be rigidly fixed to spreader assembly 14, movably fixed to spreader assembly 14, or a combination of rigid and movable fixation. Suitable examples of actuator assembly 12 components include solid shaft like elements, bar stock, tubular elements, rod-like elements, linkages, elastically-deformable members, and articulating connectors, for example. Actuator assembly 12 can be biased by a spring, resilient hinge or other means to a normal position in which spreader assembly 14 is unactuated, actuated, or at some position therebetween.

Adjustment mechanism 16 can position and/or maintain spreader assembly 14 in any one of a number of actuated states, and is provided with means for securing one or more components of actuator assembly 12 in a particular position. Such means can include a rod and stop member movably engageable along the rod, a geared mechanism, a force fit or wedge mechanism, a pivoting locking mechanism, a rotational locking mechanism, one or more clamping members, an interference fit between components of actuator assembly 12, and an interference fit between one or more components connected to and extending between the components of actuator assembly 12, for example.

Distal spreader assembly 14 can include a pair of spreading members movable away from one another by actuator assembly 12 to spread adjacent bony structures. The spreading members can be coupled to actuator assembly 12 for movement in parallel relation to one another, although non-parallel movement is also contemplated. Distal spreader assembly 14 can include a low profile arrangement in the unactuated state for insertion of the spreading members into a space between the adjacent bony structures. Such low profile arrangement can be provided by nesting the spreading members, collapsing of the spreading members, overlapping the spreading members, and/or compressing the spreading members. The spreading members of spreader assembly 14 can each be configured to conform to the profile of the bony structure of which it contacts. Each spreading member can include means for engaging the bony structure to resist movement of the spreading members relative to the bony structure. Such engagement means includes pitting, knurling, serrations, teeth, ridges, barbs, spikes, peeks and valleys, grooves, concave curvature, and convex curvature.

One embodiment of a spreader instrument 20 will be described with reference to FIGS. 2-4. This embodiment of spreader instrument 20 includes actuator assembly 21, distal spreader assembly 90 and an optional adjustment mechanism 45. Actuator assembly 21 includes a first handle 22 pivotally coupled to a second handle 24 about a fastener 26. Other coupling arrangements are also contemplated, such as an integral hinge or separate hinge mechanism. A first spring member 42 extends along first handle 22 and is coupled thereto with pin 42a. A second spring member 44 extends along second handle 24 and is coupled thereto with pin 44a. Spring members 42, 44 are leaf springs that are interconnected at their distal ends to spring bias handles 22, 24 away from one another to an unactuated position, shown in FIG. 2. Handles 22, 24 are moved to an actuated position by moving handles 22, 24 toward one another against spring members 42, 44, as shown in FIG. 3.

Adjustment mechanism 45 is provided to adjust and/or secure handles 22, 24 and thus spreader assembly 90 in any one of a number of actuated positions. Adjustment mechanism 45 includes a connecting member 46 pivotally coupled at a distal end 46b to second pin 44a. Connecting member 46 extends through an aperture of a first handle extension 22b to proximal end 46a, and pivots as handles 22, 24 move toward or away from one another. An adjustment member 48 located between handle extension 22b and proximal end 46a is movable along connecting member 46. In the illustrated embodiment, connecting member 46 is threaded and adjustment member 48 is a hand knob threadingly coupled thereto. Proximal end 46a of connecting member 46 can be non-threaded and enlarged to retain adjustment member 48 on connecting member 46. Adjustment member 48 contacts handle extension 22b to maintain handles 22, 24 and distal spreader assembly 90 in any one of a number of actuated positions. Adjustment member 48 can be threaded toward proximal end 46a of connecting member 46 in the direction opposite arrow P. This allows handles 22, 24 to move along connecting member 46 and return toward their unactuated position when released until either adjustment member 48 contacts handle extension 22b or the handles 22, 24 and spreader assembly 90 are completely unactuated. Adjustment member 48 can be threaded along connecting member 46 in the direction of arrow P toward handle extension 22b to engage or move handles 22, 24 toward one another for actuation.

Distal spreader assembly 90 includes a first spreading member 50 and a second spreading member 70. First spreading member 50 includes a proximal portion 52 attachable to actuator assembly 21. An extension member 54 extends distally from proximal portion 52. Second spreading member 70 includes a proximal portion 72 attachable to actuator assembly 21. An extension member 74 extends distally from proximal portion 72.

Figure 4:
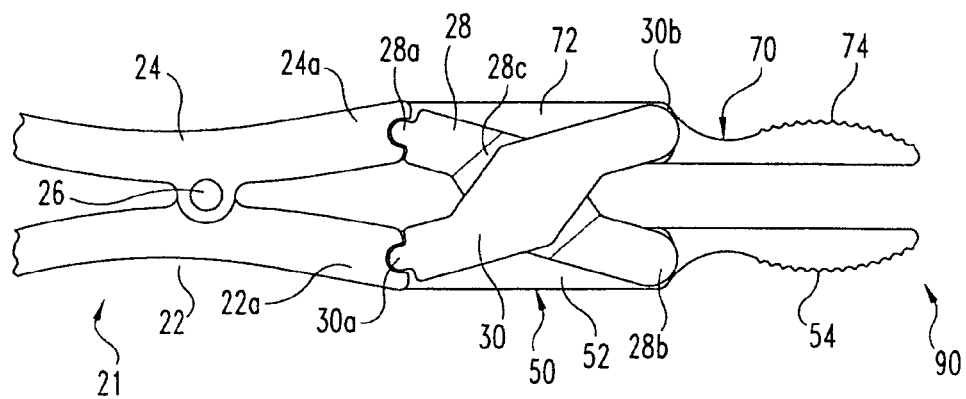
FIG. 4 is an elevation view of a portion of the side of the actuated spreader instrument opposite the side shown in FIG. 3.

As shown in FIG. 4, spreader instrument 20 is rotated 180 degrees about longitudinal axis L. First handle 22 is pivotally coupled at its distal end 22a to a proximal end 30a of a first link member 30. Second handle 24 is pivotally coupled at its distal end 24a to a proximal end 28a of a second link member 28. First link member 30 extends to a distal end 30b, and second link member 28 extends to a distal end 28b. Link members 28, 30 cross one another to form an X-shape in their actuated state as shown in FIGS. 3 and 4. Link members 28, 30 are pivotally couple to one another about central fastener 40 (FIG. 2) of actuator assembly 21. The overlapping portions of the crossed link members 28, 30 can be recessed so that the distal and proximal end portions of link members 28, 30 extend over one another, as shown with recessed portions 28c n FIG. 4 and recessed portion 30c in FIG. 3.

Proximal portion 52 of first spreading member 50 includes a proximal slot 56 through which fastener 35 extends. Proximal portion 52 further includes a distal hole 58 through which fastener 39 extends. Fastener 35 rotatably and slidably couples proximal portion 52 to actuator assembly 21 at the connection between distal end 22a of first handle 22 and proximal end 30a of first link member 30. Fastener 39 rotatably couples proximal portion 52 to distal end 28b of second link member 28. Second spreading member 70 includes a proximal portion 72 attachable to actuator assembly 21. Proximal portion 72 includes a proximal slot 76 through which fastener 33 extends. Proximal portion 72 further includes a distal hole 78 through which fastener 37 extends. Fastener 33 rotatably and slidably couples proximal portion 72 to actuator assembly 21 at the connection between distal end 24a of second handle 24 and proximal end 28a of second link member 28. Fastener 37 rotatably couples proximal portion 72 to distal end 30b of first link member 30.

When actuator assembly 21 is in an unactuated state as shown in FIG. 2, spreading members 50, 70 are positioned adjacent one another. As actuator assembly 21 is actuated by moving handles 22, 24 toward one another, spreading members 50, 70 can move away from and remain parallel during such movement. The rotatable and slotted engagement of proximal portions 52, 72 via fasteners 35, 33 in slots 56, 76, respectively, allows the relative longitudinal position between actuator assembly 21 and spreading members 50, 70 to vary in accordance with the amount of actuation provided between spreading members 50, 70.

In operation, distal ends 22a, 24a of handles 22, 24 move away from one another by the pivoting of handles 22, 24 about fastener 26. In addition, distal ends 28b, 30b of link members 28, 30 move away from one another by the pivoting of link members 28, 30 about fastener 40. This pivoting movement of the components of actuator assembly 21 causes the length of actuator assembly 21 to reduce along longitudinal axis L. Spreading members 50, 70 rotate about respective ones of the fasteners 39, 37, respectively, as distal ends 28b, 30b of link members 28, 30 are moved away from one another. Fasteners 35, 33 rotate within and move distally in respective ones of the slots 56, 76 as distal ends 22a, 24a move away from one another. The movement of fasteners 35, 33 in slots 56, 76 accommodates the reduction in length of actuator assembly 21 along axis L, while the rotation of fasteners 35, 33 in slots 56, 76 allows spreading members 50, 70 to remain parallel to one another as actuator assembly 21 is actuated and unactuated.

Figure 5:
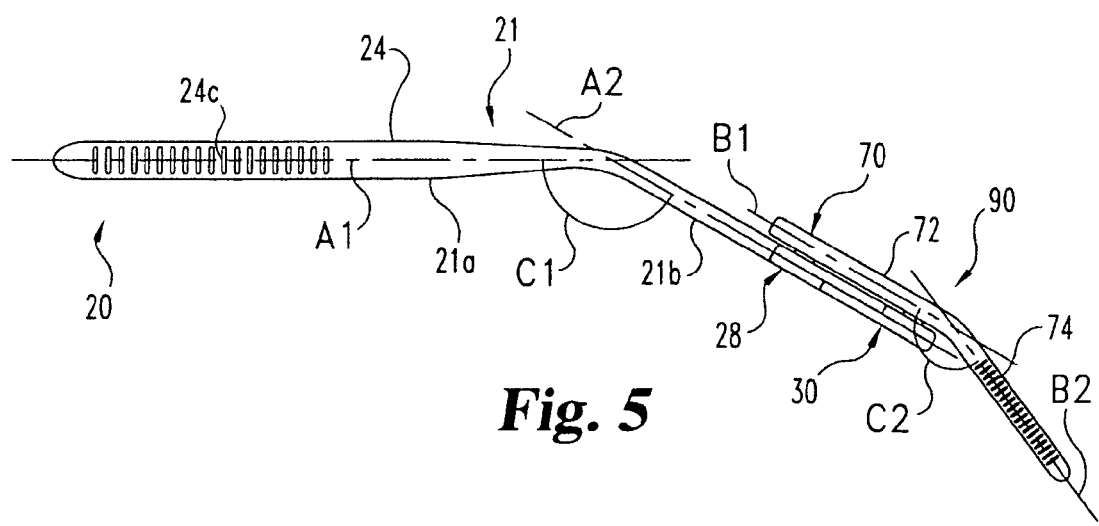
FIG. 5 is a plan view looking toward the bottom of the spreader instrument of FIG. 2.
Figure 9:
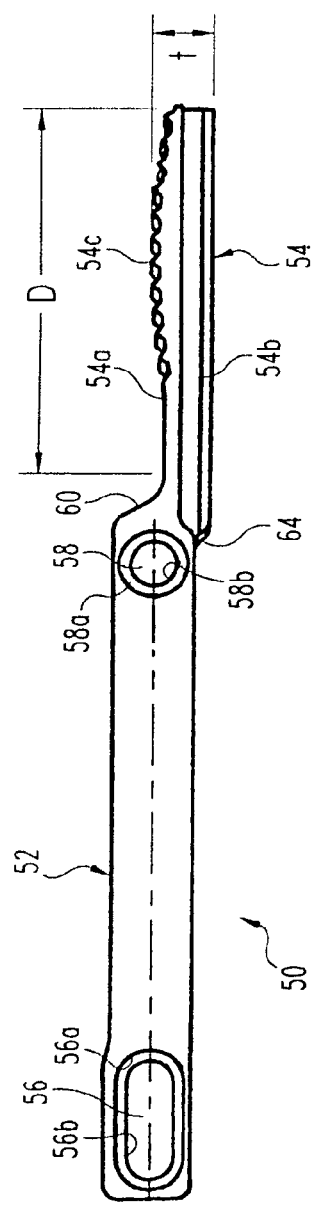
FIG. 9 is an elevation view looking at the side of a first spreading member of the distal spreader assembly of FIG. 6.
Figure 10:
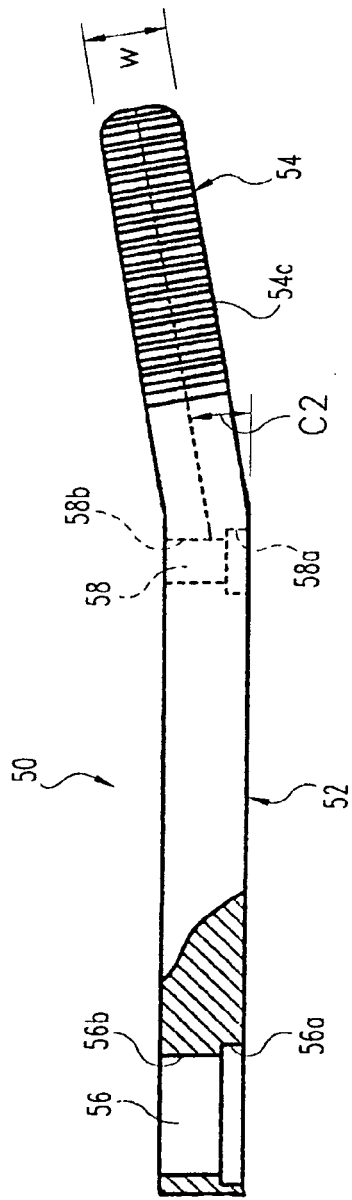
FIG. 10 is an elevation view looking at the contact surface of the spreading member of FIG. 6.
Figure 11:
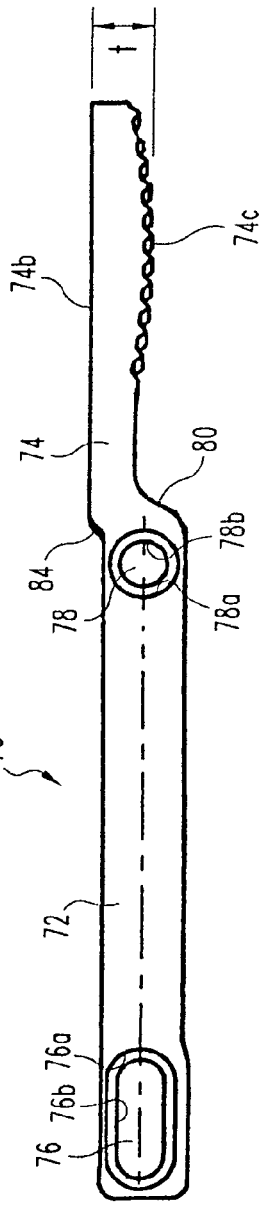
FIG. 11 is an elevation view looking at the side of the second spreading member of the distal spreader assembly of FIG. 6.
Figure 12:
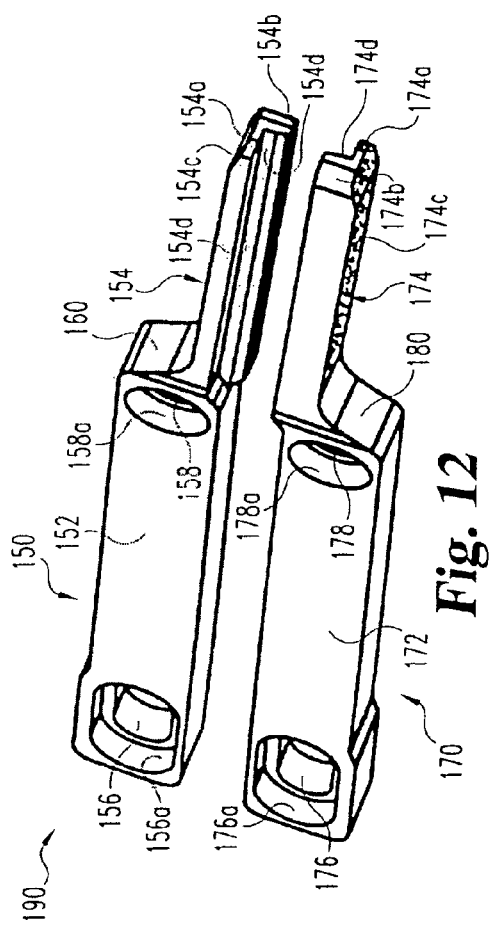
FIG. 12 is a perspective view of another embodiment of a distal spreader assembly.
Figure 13:
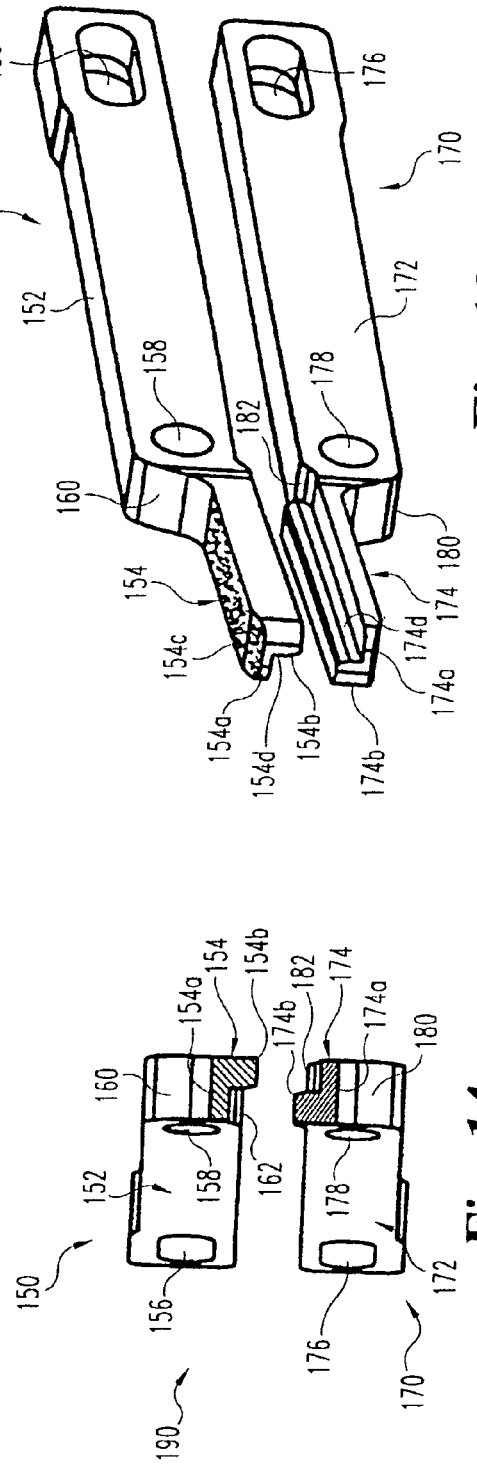
FIG. 13 is another perspective view of the distal spreader assembly of FIG. 12.
Figure 14:
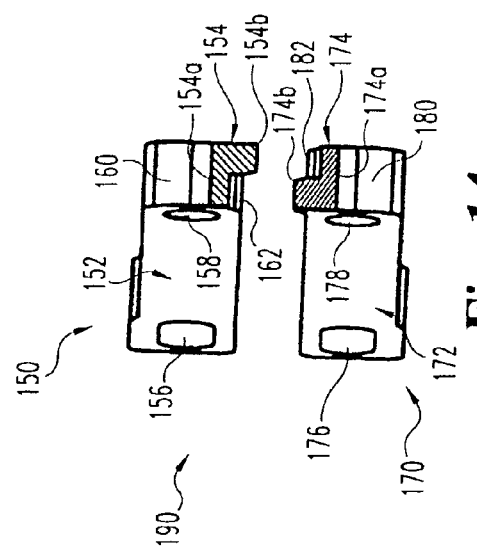
FIG. 14 is a sectional view through the spreading members of the distal spreader assembly of FIG. 12.

As shown in FIG. 5, spreader instrument 20 can be provided with angled offsets in actuator assembly 21 and spreader assembly 90 to assist in keeping spreader instrument 20 out of the way of the surgeon. In FIG. 5, handles 22, 24 for a proximal portion 21a of actuator assembly 21 extending along axis A1 and a distal portion 21b extending along axis A2. Link members 28, 30 also extend along axis A2. Axis A1 forms angle C1 with axis A2. Angle C1 can vary from 180 degrees to 90 degrees or less. It is also contemplated that angle C1 can range from 180 degrees to 135 degrees. One specific embodiment contemplates an angle C1 of 170 degrees. Another specific embodiment contemplates an angle C1 of 0 degrees Proximal portions 52, 72 of spreading members 50, 70 of distal spreader assembly 90 extend along axis B1. Proximal portions 52, 72 are coupled to one side of actuator assembly 21 such that axis B1 is offset from and extends parallel to axis A2. In one embodiment, it is contemplated that spreader assembly 90 can be coupled to the working side of spreading instrument 20 so that actuator assembly 21 is offset laterally from spreader assembly 90, providing additional space in the surgeon's approach to the operative site. Extension members 54, 74 extend along an axis B2 that forms angle C2 with axis B1. Angle C2 can vary from 180 degrees to 90 degrees or less. It is further contemplated that angle C2 can vary from 180 degrees to 135 degrees. One specific embodiment contemplates an angle C2 of 170 degrees. Another specific embodiment contemplates an angle C2 of 180 degrees.

Referring to FIGS. 6-11, spreading member 50 includes an enlarged opening 56a about slot 56 so that the head of fastener 35 can be recessed at least partially therein. The shaft of fastener 35 extends through slotted portion 56b. Similarly, spreading member 70 includes slot 76 with an enlarged opening 76a about slotted portion 76b so that the head of fastener 33 can be recessed at least partially therein. Hole 58 of spreading member 50 includes an enlarged opening 58a in which the head of fastener 39 can be recessed, and the shaft of fastener 39 extends through hole portion 58b. Similarly, spreading member 70 includes hole 78 with an enlarged opening 78a about hole portion 78b so that the head of fastener 37 can be recessed at least partially therein.

Spreading member 50 includes a concavely curved end wall 60 extending from proximal portion 52 to extension member 54. Spreading member 70 includes a concavely curved end wall 80 extending from proximal portion 72 to extension member 74. End walls 60, 80 can abut against the bony structure adjacent the space in which extension members 54, 74 are inserted to limit the insertion depth of extension members 54, 74 into the space.

Extension member 54 and extension member 74 each include a configuration that allows the extensions members 54, 74 to be positioned adjacent one another in a low profile arrangement for insertion into the space between the adjacent bony structures. Extension member 54 includes a laterally oriented flange portion 54a and a vertically oriented web portion 54b extending along flange portion 54a. Flange portion 54a includes a contact surface 54c opposite web portion 54b. Flange portion 54a and web portion 54b define a receptacle 54d. Extension member 74 includes a laterally oriented flange portion 74a and a vertically oriented web portion 74b extending along flange portion 74a. Flange portion 74a includes a contact surface 74c opposite web portion 74b. Flange portion 74a and web portion 74b define a receptacle 74d. Receptacle 74d is sized to receive web portion 54b, and receptacle 54d is sized to receive web portion 74b, allowing extension members 54, 74 to be placed in a nested configuration when spreader instrument 20 is unactuated and spreading members 50, 70 are placed against or adjacent to one another.

Flange portion 54a includes a ramped surface 62 opposite contact surface 54c that transitions into proximal portion 52, and web portion 54b includes a ramped surface 64 opposite contact surface 54c that transitions into proximal portion 52. Similarly, flange portion 74a includes a ramped surface 82 opposite contact surface 74c that transitions into proximal portion 72, and web portion 74b includes a ramped surface 84 opposite contact surface 74c that transitions into proximal portion 72. The ramped transition surfaces facilitate the nesting relationship between extension members 54, 74 when proximal portions 52, 72 are positioned adjacent one another.

In one form, spreading member 50 and spreading member 70 are positioned adjacent one another and in contact with one another along their entire length in the low profile position. In another form, at least extension members 54, 74 are positioned adjacent to one another and in contact along their entire length in the low profile orientation. This low profile orientation facilitates positioning of spreading members 50, 70 as far as possible in the disc space to obtain an even distraction or spreading of the adjacent vertebrae in the distal and proximal regions of the disc space.

Contact surfaces 54c, 74c can have a profile that maximizes the surface area contact with the adjacent bony structure. For example, contact surface 54c, 74c can have a convex profile that matches the geometry of the portion of the endplates of vertebrae V1 and V2 along which the extension members 54, 74 are positioned, as shown in FIGS. 2 and 3. Such matching geometry maintains extension members 54, 74 in position relative to the vertebral endplate, and also spreads the distraction or spreading load over a greater area of the bony structure, reducing potential damage to the bony structure that might be caused by distraction or spreading forces concentrated on portions of the adjacent endplate. The matching geometry also provides a self-centering effect to assist in proper positioning of extension members 54, 74 in the space relative to the bony structures.

Contact surfaces 54c, 74c can be smooth or have surface features that engage the bony structure, such as the grooves forming the ridges shown in FIGS. 2-11 that extend transversely to convex curvature of the respective bone contacting surface. Examples of other surface features include pitting, knurling, serrations, teeth, ridges, barbs, spikes, peeks and valleys, grooves, concave curvature, and convex curvature, for example.

In one specific embodiment, each extension member 54, 74 can be provided with a maximum thickness t of 6 millimeters, and receptacles 54d, 74d each have a depth of 3 millimeters. Thus, extension members 54, 74 can have an overall maximum height of 9 millimeters between contact surfaces 54c, 74c when spreader assembly 90 is in its unactuated position and spreading members 50, 70 are nested relative to one another. Thus, in the specific illustrated embodiment, the nested relationship provides at least a 25% reduction in height along the entire length of extension members 54, 74 than would be provided in a non-nested relationship. Extension members 54, 74 can have a width W of 8 millimeters, and web portions 54b, 74b occupy half of width W. Extension members 54, 74 can also be provided with a length D of 40 millimeters, or other length D such that the extension members 54, 74 extend across a substantial portion of a disc space providing even and complete separation of the adjacent vertebrae. It is to be understood that other embodiments contemplate other maximum heights, widths and lengths for extension members 54, 74.

The moment of inertia and section modulus provided by extension members 54, 74 maintains deflection of extension members 54, 74 within acceptable limits even with long lengths D for extensions members 54, 74. Accordingly, extension members 54, 74 can be provided with length D that extends substantially across the adjacent vertebral endplate, and uniform distraction or spreading of the vertebrae and force distribution along the vertebrae can be achieved. The low profile, nested configuration of extension members 54, 74 in the unactuated position facilitates insertion into a collapsed or partially collapsed disc space or through a small opening to the space between adjacent bony structures.

Referring now to FIGS. 12-17, another embodiment of a distal spreader assembly 190 is provided. Spreader assembly 190 can be mounted to actuator assembly 21 such as discussed above with respect to spreader assembly 90. Spreader assembly 190 includes a first spreading member 150 and a second spreading member 170. First spreading member 150 includes a proximal portion 152 attachable to actuator assembly 21. An extension member 154 extends distally from proximal portion 152. Second spreading member 170 includes a proximal portion 172 attachable to actuator assembly 21. An extension member 174 extends distally from proximal portion 172.

Proximal portion 152 includes a proximal slot 156 through which fastener 35 extends. Proximal portion 152 further includes a distal hole 158 through which fastener 39 extends. Fastener 35 rotatably and slidably couples proximal portion 152 to actuator assembly 21 at the connection between distal end 22a of first handle 22 and proximal end 30a of first link member 30. Fastener 39 rotatably couples proximal portion 152 to distal end 28b of second link member 28. Second spreading member 170 includes a proximal portion 172 attachable to actuator assembly 21. Proximal portion 172 includes a proximal slot 176 through which fastener 33 extends. Proximal portion 172 further includes a distal hole 178 through which fastener 37 extends. Fastener 33 rotatably and slidably couples proximal portion 172 to actuator assembly 21 at the connection between distal end 24a of second handle 24 and proximal end 28a of second link member 28. Fastener 37 rotatably couples proximal portion 172 to distal end 30b of first link member 30.

Spreading member 150 includes an enlarged opening 156a about slot 156 so that the head of fastener 35 can be recessed at least partially therein. The shaft of fastener 35 extends through a slotted portion 156b. Similarly, spreading member 170 includes slot 176 including an enlarged opening 176a about slotted portion 176b so that the head of fastener 33 can be recessed at least partially therein. Hole 158 of spreading member 150 includes an enlarged opening 158a in which the head of fastener 39 can be recessed, and the shaft of fastener 39 extends through hole portion 158b. Similarly, spreading member 170 includes an enlarged opening 178a about hole 178 so that the head of fastener 37 can be recessed at least partially therein with the shaft extending through hole portion 178b.

When actuator assembly 21 is in an unactuated state as shown in FIG. 2, spreading members 150, 170 are positioned adjacent one another. As actuator assembly 21 is actuated by moving handles 22, 24 toward one another, spreading members 150, 170 can move away from and remain parallel during such movement in the manner discussed above with respect to spreader assembly 90, as shown in FIG. 3.

Spreading member 150 includes a concavely curved end wall 160 extending from proximal portion 152 to extension member 154. Spreading member 170 includes a concavely curved end wall 180 extending from proximal portion 172 to extension member 174. End walls 160, 180 can abut against the bony structure adjacent the space in which extension members 154, 174 are inserted to limit the insertion depth of extension members 154, 174 into the space.

Extension member 154 and extension member 174 each include a configuration that allows the extensions members 154, 174 to be positioned adjacent one another in a low profile arrangement for insertion into the space between the adjacent bony structures. Extension member 154 includes a lateral flange portion 154a and a web portion 154b extending along flange portion 154a. Flange portion 154a includes a contact surface 154c opposite web portion 154b. Flange portion 154a and web portion 154b define a receptacle 154d. Extension member 174 includes a flange portion 174a and a web portion 174b extending along flange portion 174a. Flange portion 174a includes a contact surface 174c opposite web portion 174b. Flange portion 174a and web portion 174b define a receptacle 174d. Receptacle 174d is sized to receive web portion 154b, and receptacle 154d is sized to receive web portion 174b, allowing extension members 154, 174 to be placed in a nested configuration when spreader instrument 20 is unactuated and spreading members 150, 170 are placed against or adjacent to one another. Web portions 154b, 174b are provided with a uniform height along the respective flange portion 154a, 174a, allowing the height of the nested extension members 154, 174 to be minimized along the entire length thereof.

Flange portion 154a includes a ramped surface 162 opposite contact surface 154c that transitions into proximal portion 152, and web portion 154b includes a ramped surface 164 opposite contact surface 154 that transitions into proximal portion 152. Flange portion 174a includes a ramped surface 182 opposite contact surface 174c that transitions into proximal portion 172, and web portion 174b includes a ramped surface 184 opposite contact surface 174c that transitions into proximal portion 172. The ramped transition surfaces facilitate the nesting relationship between extension members 154, 174.

Contact surfaces 154c, 174c can include a relatively flat profile along flange portions 154a, 174a. In one embodiment, contact surfaces 154c, 174c includes a number of surface features that include pits formed by a chemical photo-etching process. The process can produce many various patterns, ranging from a very fine surface roughness to a very coarse surface roughness. The patterns of etching can be controlled by using computer-generated negatives of the desired pattern. By controlling the surface area affected by the photo-etching and the etching depth, the strength of the respective extension member 154, 174 can be maintained in close proximity to its original, unetched strength. In comparison, an extension member including surface features formed by mechanical cutting or abrasion requires a greater thickness to maintain the same bending strength after placement of the surface features than does an extension member with chemically etched surface features. Thus, the thickness of flange portions 154a, 174a can be minimized to provide a low profile spreader assembly with bone engagement structures on the spreading member for insertion into small spaces between adjacent bony structures.

In one specific embodiment, each extension member 154, 174 can be provided with a thickness t of 3.5 millimeters, and recesses 154d, 174d each have a depth of 2 millimeters. Thus, extension members 154, 174 can have an overall height of 5 millimeters between contact surfaces 154c, 174c when spreader assembly 190 is in its unactuated position and spreading members 150, 170 are nested relative to one another. Thus, in the specific illustrated embodiment, the nested relationship provides at least a 28% reduction in height than would be provided in a non-nested relationship. In the specific embodiment, extension members 154, 174 can have a width W of 5 millimeters, and web portions 154d, 174d occupy half of width W. Extension members 154, 174 can also be provided with a length D of 32 millimeters, or other length D such that the extension members 154, 174 extend across a substantial portion of a disc space providing even and uniform separation of the adjacent vertebrae across the disc space. It is to be understood that other embodiments contemplate other maximum heights, widths and lengths for extension members 154, 174.

The moment of inertia and section modulus provided by extension members 154, 174 maintains deflection of extension members 154, 174 within acceptable limits even with long lengths D. The low profile unactuated height of extension members 154, 174 and their parallel relationship allow extension members to be completely inserted in the space between the adjacent bony structures before distraction or spreading. The controlled deflection of extension members 154, 174 provides uniform spreading or distraction of the vertebrae across the disc space, facilitating endplate and disc space preparation and implant insertion.

Referring back to FIGS. 2-3, techniques employing the spreader instrument will be described with reference to spreader instrument 20, it being understood that the techniques described also have application with the other embodiments discussed herein and in surgical procedures other than spinal surgery. In FIG. 2 spreader instrument 20 has a reduced profile configuration for insertion into a collapsed disc space D between vertebrae V1 and V2. Actuator assembly 21 is actuated to move spreading members 50, 70 away from one another in parallel relation. In one embodiment, actuator assembly 21 moves spreading members 50, 70 away from one another in parallel relation while actuator assembly 21 simultaneously moves longitudinally relative to the spreading members 50, 70. It should be understood, however, that aspects of the invention contemplate that the spreading members are not moved parallel to one another and/or are not parallel to one another.

The spreading members 50, 70 contact an endplate of a respective one of the vertebrae V1 and V2. Spreading members 50, 70 are moved further away from one another with actuator assembly 21 to restore collapsed disc space D from its collapsed height H1 to a restored height H2. Thereafter the surgeon can insert instruments and the like into disc space D to remove bone material, disc material and the like to prepare the disc space for subsequent procedures, such as the insertion of an interbody device, fusion device, graft material, or artificial disc, for example. Spreader instrument 20 can maintain disc space distraction during such procedures. Since, contact surfaces 54c, 74c occupy relatively small areas of the vertebral endplates, it is contemplated that the entire procedure can be conducted with spreader instrument 20 in the disc space. It is further contemplated that spreader instrument 20 can be easily and quickly repositioned in the disc space for completion of procedures in the areas previously occupied by the spreader instrument.

One specific application contemplates distracting or spreading adjacent vertebrae of the spine. Any number of approaches to the spine are contemplated, including anterior, posterior, lateral, postero-lateral, antero-lateral approaches, for example, and also in minimally invasive and open surgical procedures. Aspects of the spreader instrument embodiments discussed can be employed in spreader instruments adapted for endoscopic, laparoscopic, and/or thoracoscopic procedures. The spreader instrument can also be employed to spread adjacent bony structures in locations other than the spine.

In one embodiment, the spreading members are provided with a ceramic coating. A ceramic coating can provide a low friction surface treatment that reduces or eliminates glare from the distal spreader assembly, enhancing surgeon viewing of the operative site. It is further contemplated that the spreading instruments can be made from any material acceptable for fabrication of surgical instruments.

Another embodiment of a spreader instrument 220 will be described with reference to FIGS. 17-20. This embodiment of spreader instrument 220 includes an actuator assembly 221, a distal spreader assembly 290 and an optional adjustment mechanism 245. Actuator assembly 221 includes a first handle 222 pivotally coupled to a second handle 224 about a fastener 226. A first spring member 242 extends between first handle 222 and second handle 224 along and about a pin 244. Spring member 242 is a coil spring that biases handles 222, 224 away from one another so that spreader assembly 290 of spreader instrument 220 is biased to a normally closed position, as shown in FIG. 18. Handles 222, 224 are moved to an actuated position by moving handles 222, 224 toward one another against spring member 242, compressing spring member 242 along pin 244 as shown in FIG. 19.

Adjustment mechanism 245 is provided to adjust and/or secure handles 222, 224 and thus spreader assembly 290 in any one of a number of actuated positions. Adjustment mechanism 245 includes pin 244 pivotally connected to handle 222 and extending through handle 224. Spring member 242 extends about the portion of pin 244 between handles 222, 224. An adjustment member 248 located on the end of pin 244 extending through handle 224 is movable along pin 244 to adjust and/or maintain the relative positioning between handles 222, 224. In the illustrated embodiment, pin 244 can be threaded and adjustment member 248 can be a hand knob threadingly coupled thereto. The outer end of pin 244 can be non-threaded and enlarged to retain adjustment member 248 on pin 244.

Adjustment member 248 can contact second handle 224 to maintain handles 222, 224 and distal spreader assembly 290 in any one of a number of actuated positions. Adjustment member 248 can be threaded toward the direction opposite arrow P to allow handles 222, 224 to return toward their unactuated position until either adjustment member 248 contacts handle 224 or the handles 222, 224 and spreader assembly 290 are completely unactuated. Adjustment member 248 can be threaded along pin 244 in the direction of arrow P toward handle 224 to maintain an actuated position or move handles 222, 224 toward one another for actuation.

First handle 222 is pivotally coupled at its distal end 222a to a proximal end of a first link member 230. Second handle 224 is pivotally coupled at its distal end 224a to a proximal end of a second link member 228. Link members 228, 230 cross one another to form an X-shape in their actuated state as shown in FIGS. 19 and 20. Link members 228, 230 are pivotally coupled to one another about central fastener 240 of actuator assembly 221. The overlapping portions of the crossed link members 228, 230 can be recessed so that the distal and proximal end portions of link members 228, 230 can extend over and be aligned with one another, as shown in FIG. 21.

Distal spreader assembly 290 includes a first spreading member 250 and a second spreading member 270. First spreading member 250 is attachable to a first coupling member 252 of actuator assembly 221. Second spreading member 270 is attachable to a second coupling member 272 of actuator assembly 221. Coupling member 252 includes a distal slot 256 through which fastener 235 extends. Coupling member 252 further includes a proximal hole through which fastener 239 extends. Fastener 235 rotatably and slidably couples coupling member 252 to a distal end of second link member 228 of actuator assembly 221. Fastener 239 rotatably couples coupling member 252 to a proximal end of first link member 230. Second coupling member 272 includes a distal slot 276 through which fastener 233 extends. Coupling member 272 further includes a proximal hole through which fastener 237 extends. Fastener 233 rotatably and slidably couples coupling member 272 to a distal end of first link member 230. Fastener 237 rotatably couples coupling member 272 to a proximal end of second link member 228.

When actuator assembly 221 is in an unactuated state as shown in FIG. 18, spreading members 250, 270 are positioned adjacent one another. As actuator assembly 221 is actuated by moving handles 222, 224 toward one another, spreading members 250, 270 can move away from one another and remain parallel during such movement. The rotatable and slotted engagement of coupling members 252, 272 via fasteners 235, 233 in slots 256, 276, respectively, allows the relative longitudinal position between actuator assembly 221 and spreading members 250, 270 to vary in accordance with the amount of actuation provided, and for spreading members 250, 270 to remain parallel to one another during such movement. It should be understood, however, that other actuator assemblies 221 are contemplated, including those that provide non-parallel movement of spreading members 250, 270. Actuator assembly 221 could also be configured to move spreading members 250, 270 through, for example, a scissors coupling arrangement between handles 222, 224, a gear rack mechanism, or other actuator assembly arrangement discussed herein.

In operation, the distal ends 222a, 224a of handles 222, 224 move away from one another by the pivoting of handles 222, 224 about fastener 226. In addition, the distal ends of link members 228, 230 move away from one another by the pivoting of link member 228, 230 about fastener 240. This pivoting movement of the components of actuator assembly 221 causes the length of spreader instrument 220 to reduce along longitudinal axis L. Coupling members 252, 272 rotate about respective ones of the fasteners 239, 237, respectively, as spreading members 250, 270 are moved away from one another. Fasteners 235, 233 rotate within and move proximally in respective ones of the slots 256, 276 as spreading members 250, 270 move away from one another. The movement of fasteners 235, 233 in slots 256, 276 accommodates the reduction in length of actuator assembly 221 along axis L, while the rotation of fasteners 235, 233 in slots 256, 276 and the rotation of fasteners 239, 237 allows spreading members 250, 270 to remain parallel to one another as actuator assembly 221 is actuated and unactuated.

In the unactuated position of FIG. 18, spreading members 250, 270 are positioned adjacent one another, and have an overall height H3 that allows insertion of distal extension members 262, 282 of spreading members 250, 270, respectively, into a spinal disc space or corpectomy space between adjacent vertebrae. In an actuated state, spreading members 250, 270 can be separated so that a height H4 is provided between distal extension members 258, 278. Height H4 can correspond to a desired disc space height prior to disc space preparation, vertebral body preparation, and/or implant insertion. The configuration of actuator assembly 221 contemplates that handles 222, 224 are moved toward one another to move spreading members 250, 270 away from one another, which can limit the maximum distraction or separation height H4 when the handles contact or are adjacent one another.

Spreading members 250, 270 can be removably coupled to coupling members 252, 272, respectively so that spreading members 250, 270 can be readily interchanged with, for example, spreading members having different sizes and/or configurations. For example, as shown in FIG. 20, spreading members 350, 370 are attached to actuator assembly 221 and provide a maximum distraction height H5 between distal extension members 362, 382. Height H5 is greater than height H4 since each spreading member 350, 370 is provided with a stepped region 354, 384, each of which includes a height H6. Thus, the amount of distraction available with spreading members 350, 370 is greater than that provided with spreading members 250, 270 by two times height H6. Spreading members with a stepped region can be employed in, for example, corpectomy procedures where the spreading distance needed between the spreading members is greater than that required in disc space procedures.

In one specific example, selecting one spreading member with a stepped region including a height H6 provides a 15 millimeter spacing between the spreading members when the other spreading member includes no stepped region. If desired, the other spreading member can be replaced with a second spreading member including a stepped region including a height H6 that provides an additional 15 millimeter spacing between the spreading members. Thus, an overall spacing of 30 millimeters is provided between the spreading members. The ability to select and employ spreading members with stepped regions of various heights, or with no stepped region, facilitates use of the spreading instrument in corpectomy procedures and other procedures requiring additional space or separation between the adjacent bony structures may be required.

As shown in FIG. 21, actuator assembly 221 can be provided with a linear configuration along its length. Spreading members 250, 270 can be provided in a generally U-shaped configuration. For example, spreading member 270 includes a pair of distal extension members 282, 284 extending from a body portion 271. Spreading member 250 can be similarly provided with a first distal extension member (not shown) below and aligned with distal extension member 284, and a second distal extension member 262 below and aligned with distal extension member 282. Each of the spreading members 250, 270 of distal spreader assembly 290 can be offset to one side of actuator assembly 221 with, for example, an offset portion 274 extending between body portion 271 and a coupling portion 284 engaged with coupling member 272. Similarly, spreading member 250 can include an offset portion extending between a body portion and a coupling portion 264 engaged with coupling member 252. The offset of actuator assembly 221 relative to the spreading members of spreader assembly 290 facilitates access for disc space preparation, vertebral body preparation and implant insertion between the spreading members 250, 270 while spreading members 250, 270 are positioned in the space between vertebrae.

It is further contemplated that each of the handless 222, 224 can be provided with a distal portion 222c, 224c and a proximal portion 222b, 224b, respectively. Proximal portions 222b, 224b can be pivotally coupled to respective ones of the distal portions 222c, 224c about pins 230, 231, respectively. Pins 230, 231 can be configured to lock proximal portions 222b, 224b in the position shown in FIG. 20. When pins 230, 231 are pressed, proximal portions 222b, 224b can be pivoted about their connection with distal portions 222c, 224c in the direction of arrow 229 and away from spreader assembly 290 to further facilitate access to the operative site.

In FIGS. 22-41 various embodiment spreading members are provided. These spreading member embodiments and the spreading member embodiments discussed above can be employed with any of the actuator assembly embodiments or configurations discussed herein. It is further contemplated that spreading member embodiments could be removably attached to an actuator assembly so that spreading members having various configurations and/or distraction characteristics can be readily employed by the surgeon during the surgical procedure or for different surgical procedures with the same instrument set or actuator assembly. It is further contemplated that the spreading member embodiments could be a permanent and/or integral portion of the spreading instrument.

Referring now to FIGS. 22-25, another embodiment spreading member 400 is provided that is attachable to, for example, actuator assembly 221. Spreading member 400 includes a body portion 402 and a proximal coupling portion 404 offset from body portion 402 by offset portion 424. A first extension member 406 and a second extension member 408 extend distally from body portion 402. Body portion 402 further includes a proximal end wall 421 and an opposite distal end wall 422 having a concave surface profile configured to reside against or along the convex curvature of an adjacent vertebral body. Body portion 402 includes an outer surface 403 and an opposite inner surface 405 oriented toward the other spreading member when assembled with the actuator assembly.

Outer surface 403 and inner surface 405 are spaced from one another to provide a thickness or depth to body portion 402 that limits deflection upon application of a spreading load to the adjacent bony structure. For example, extension member 406 is spaced laterally from the connection of spreading member 400 with the actuator assembly 221. Thus, extension member 406 is cantilevered laterally relative to extension member 408 by body portion 402. Loads applied by extension member 406 will tend to bend or deflect body portion 402 such that extension members 406, 408 do not remain aligned with one another. Body portion 402 is provided with a thickness between outer surface 403 and inner surface 405 that limits the deflection of extension member 406 under the spreading loads to be encountered so that extension members 406, 408 remain aligned with one another to facilitate precise endplate preparation and implant insertion.

A guide member 410 extends along and forms an extension of the inner surface 405 of body portion 402 between a leading end 411 and a trailing end 412. Leading end 411 is positioned distally of body portion 402 and extends between extensions 406, 408. Trailing end 412 is positioned proximally of body portion 402. In the illustrated embodiment, guide member 410 has a flat, plate-like surface profile opposite body portion 402. As discussed further below, guide member 410 facilitates placement of disc space preparation instruments and implants between adjacent spreading members employing guide members 410.

First extension member 406 and second extension member 408 are spaced by a distance W1, and each extension member 406, 408 can be provided with a width W3. In one embodiment, spreading member 400 is adapted for an anterior approach to the lumbar spine, and width W1 can be about 27 millimeters and width W3 can be about 3.5 millimeters. Other widths W1 and W3 are contemplated for anterior approaches to the lumbar spine, and for other approaches to the spine, and for approaches to other anatomical structures. Extension members 406, 408 can be provided with a tapered leading end to facilitate insertion into the spinal disc space, and a height that tapers from body portion 402 to the leading end thereof. Extension members 406, 408 extend along and below inner surface 405 of body portion 402 as shown in FIGS. 22-23, and define a space therebetween that can receive instruments and/or implants.

Each of the extension members 406, 408 can be provided with bone engaging features, such as teeth 414 shown in FIG. 25. In the illustrated embodiment, three teeth 414 are provided on each extension member 406, 408. Teeth 414 are located so that when extension members 406, 408 are positioned in a spinal disc space and leading end wall 422 of body portion 402 is adjacent to or in contact with the vertebral body, teeth 414 can bite into or engage the cortical rim of the adjacent vertebral endplate as spreader instrument 220 is actuated to spread the adjacent vertebrae. Teeth 414 can anchor the spreader instrument to the vertebrae and resist movement of the spreader instrument relative to the vertebrae during the surgical procedure. In the illustrated embodiment, teeth 414 are V-shaped with a sharp outer end to penetrate into the adjacent bony structure.

Coupling portion 404 includes proximally opening channel having an entry portion 416 and a locking member receiving portion 418. A locking member, such as locking members 253, 273 shown in FIGS. 18-21, include a first portion positionable through entry portion 416 and a larger, second portion positionable in receiving portion 418. The larger portion is too large to pass through entry portion 416. When it is desired to engage spreading member 400 to an actuator assembly, locking member 253, for example, can be pressed downwardly so that its larger first portion is located out of the insertion path of coupling portion 404 into coupling member 252. The smaller portion of locking member 253 is located in the insertion path, and entry portion 416 can slide over the smaller portion until the smaller portion of locking member 253 is positioned in receiving portion 418 and the larger portion is aligned with receiving portion 418. Locking member 253 is then released and spring-biased to return the larger portion into receiving portion 418, providing an interference fit therewith and locking spreading member 400 to actuator assembly 221.

Figure 27:
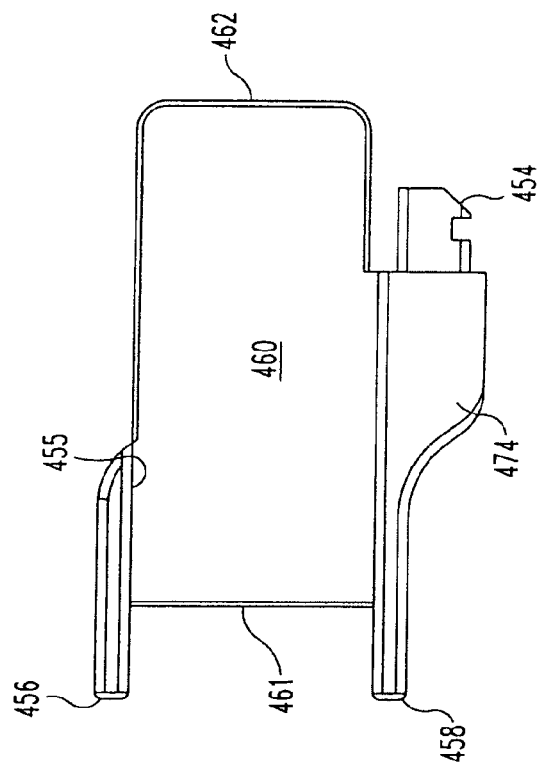
FIG. 27 is a bottom plan view of the spreading member of FIG. 26.
Figure 26:
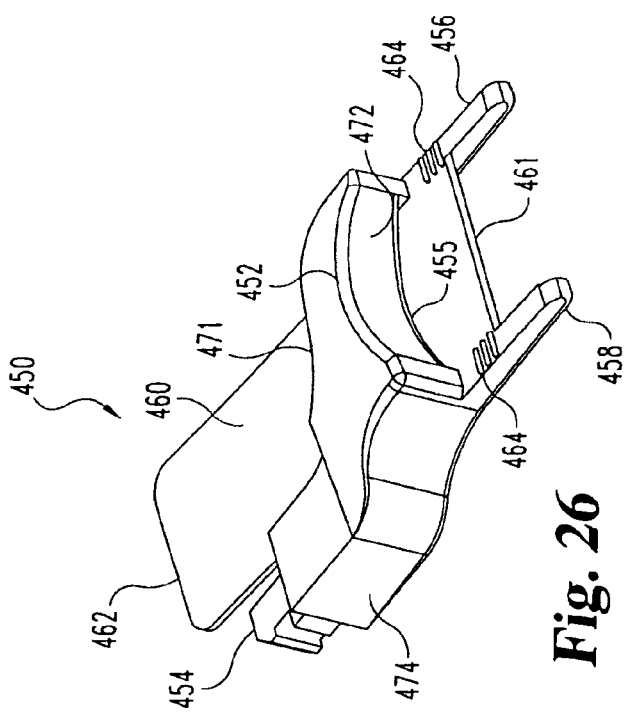
FIG. 26 is a perspective view of another embodiment spreading member useable with, for example, the spreader instrument of FIG. 18.

In FIGS. 26 and 27 there is shown another embodiment spreading member 450 attachable to a spreader instrument, such as, for example, spreader instrument 220. Spreading member 450 can be similar to spreading member 400 discussed above, and includes a body portion 452 having extension members 456, 458 extending from distal end wall 472 adjacent inner surface 455 of body portion 452. An offset portion 474 extends between body portion 452 and a coupling portion 454. Extension members 456, 458 can be provided with bone engaging features 464.

A guide member 460 extends between a leading end 461 located distally of distal end wall 472 and an opposite trailing end 462 located proximally of proximal wall 471. When compared to guide member 410 above, guide member 460 extends proximally a greater distance to provide a greater surface area along which to guide disc space preparation instruments and/or implant insertion instruments. In each embodiment, leading ends 411, 461 of guide members 410, 460 can extend into the disc space at least along the cortical rim of the adjacent vertebra. For spreading member 400, trailing end 412 can be spaced about 42.5 millimeters from leading end 411. For spreading member 450, trailing end 462 can be spaced about 60 millimeters from leading end 461. Other lengths between the leading ends and trailing ends of guide members 410, 460 are also contemplated, ranging from 7 millimeters to 80 millimeters or more, for example.

Figure 28:
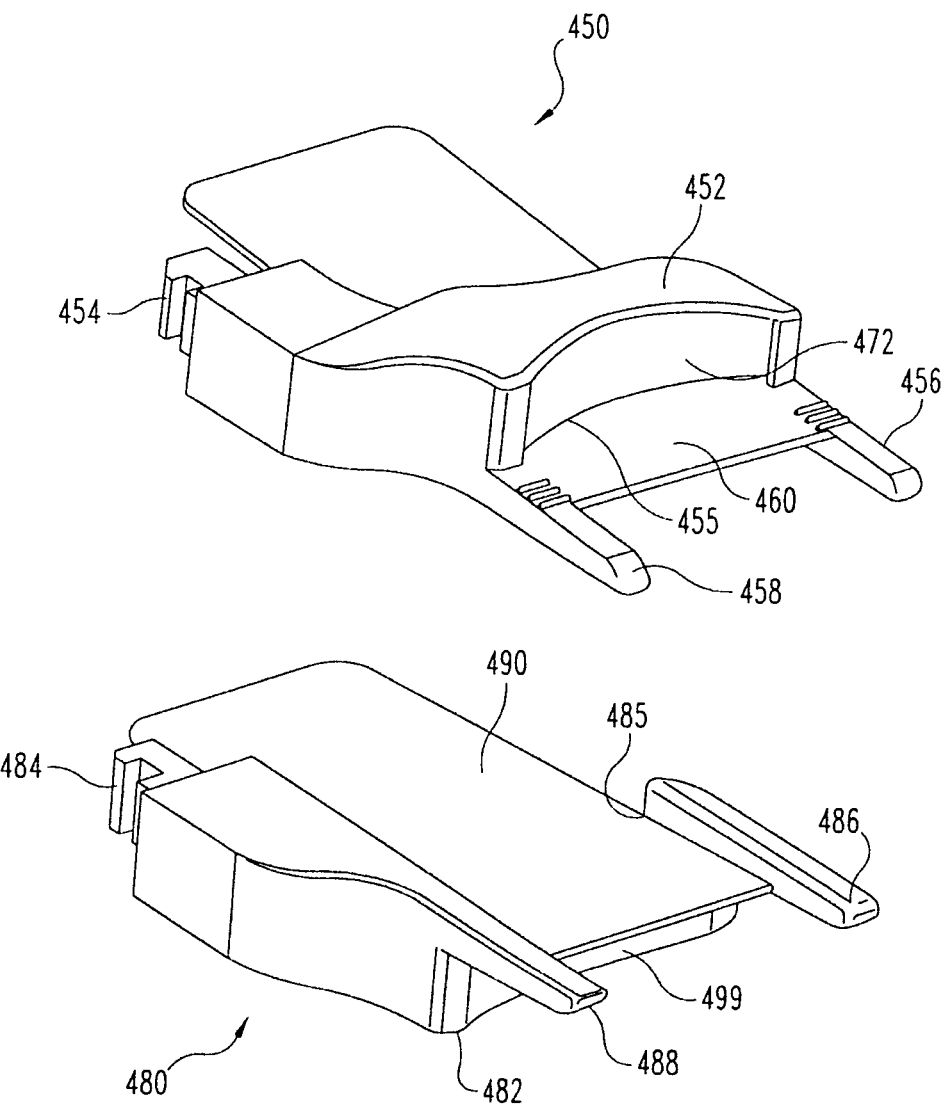
FIG. 28 is a perspective view of a pair of the spreading members of FIGS. 26 and 27 in an operative orientation relative to one another.

In FIG. 28 a pair of spreading members 450, 480 are shown separated from one another in an actuated position without an actuator assembly. Spreading member 480 is a mirror image of spreading member 450, and includes a body portion 482 having a distal end wall 499 and a pair of extension members 486, 488 extending distally from distal end wall 499. A coupling portion 484 extends proximally from body portion 452. Implants and implant insertion instruments can be guided into the disc space between spreading members 450, 480 along the flat surfaces of guide members 460, 490 adjacent the inner surfaces 455, 485.

Figure 29:
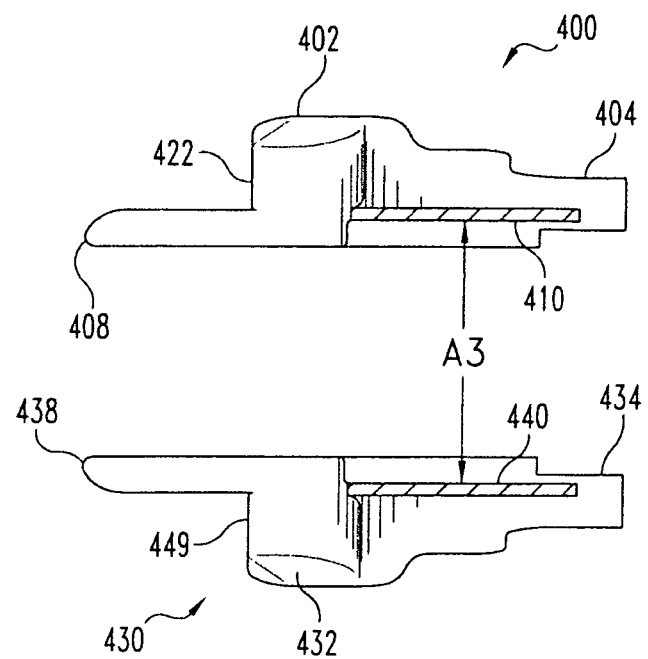
FIG. 29 is an elevation view in partial section of one operative orientation for a pair of the spreading members shown in FIGS. 22-25.
Figure 30:
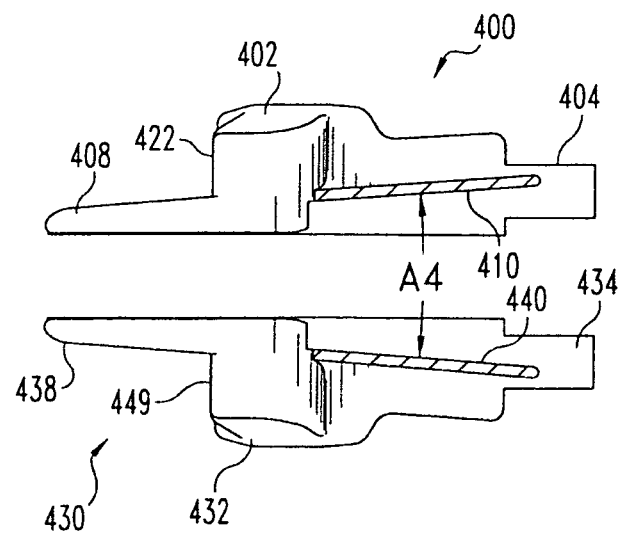
FIG. 30 is an elevation view of another operative orientation for a pair of the spreading members shown in FIGS. 22-25.

In FIG. 29 a pair of spreading members 400, 430 are shown in partial section through guide members 410, 440. Spreading members 400, 430 are separated from one another in an actuated positioned without an actuator assembly. Spreading member 430 is a mirror image of spreading member 400, and includes a body portion 432 having a distal end wall 449 and a pair of extension members (only extension member 438 shown) extending distally from distal end wall 449. A coupling portion 434 extends proximally from body portion 432. Implants and implant insertion instruments can be guided into the disc space along the flat surfaces of guide members 410, 440, which form angle A3 therebetween. In the illustrated embodiment, angle A3 is 0 degrees for parallel endplate preparation and implant insertion. In FIG. 30, angle A4 is formed between guide members so that the spacing between guide members 410, 440 tapers distally for lordotic endplate preparation, implant insertion and restoration. In one embodiment, angle A4 can be 8 degrees. Other angles are also contemplated based on the desired angle between the adjacent vertebral endplates.

Figure 31:
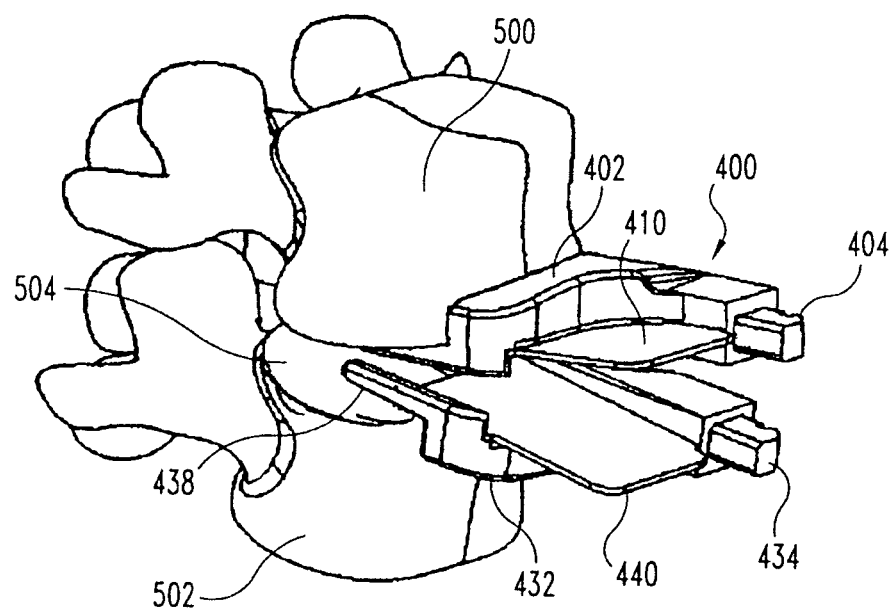
FIG. 31 is a perspective view of the spreading members of FIG. 30 positioned in a disc space between adjacent vertebrae of the spinal column.
Figure 32:
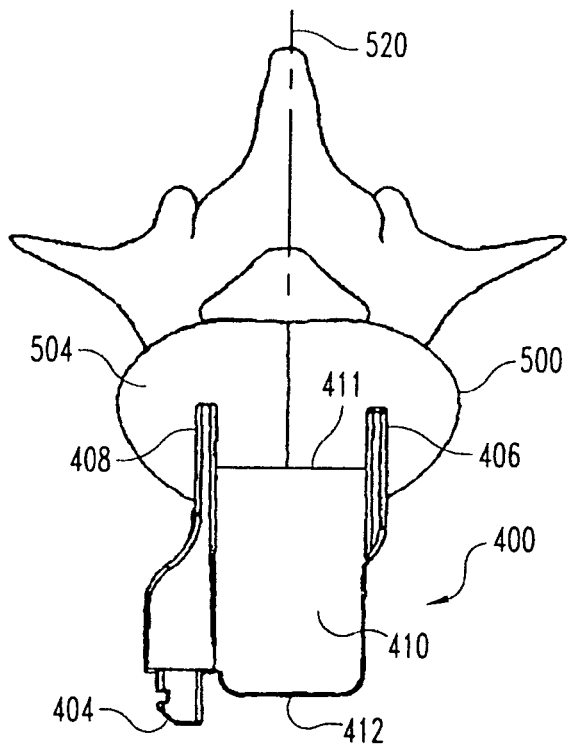
FIG. 32 is a plan view looking toward the bottom of the upper spreading member of FIG. 31 positioned in the disc space.

When positioned adjacent the spinal column, as shown in FIGS. 31 and 32, distal end walls 422, 449 of spreading members 400, 430 can abut the adjacent vertebral body 500, 502, respectively, with the extension members 406, 408 of spreading member 400 and the corresponding extension members of spreading member 430 in the spinal disc space 504. Guide members 410, 440 have their leading ends, such as leading end 411 shown in FIG. 32, extending into the disc space 504 while trailing end 412 is positioned proximally of the vertebral bodies 500, 502. The portion of the guide member extending into the disc space can protect the implant and/or the outer cortical bone from damage during insertion of the implant. Extension members 406, 408 can be centered about the sagittal plane 520, or can be offset for an oblique approach or multiple approaches to the disc space.

Figure 33:
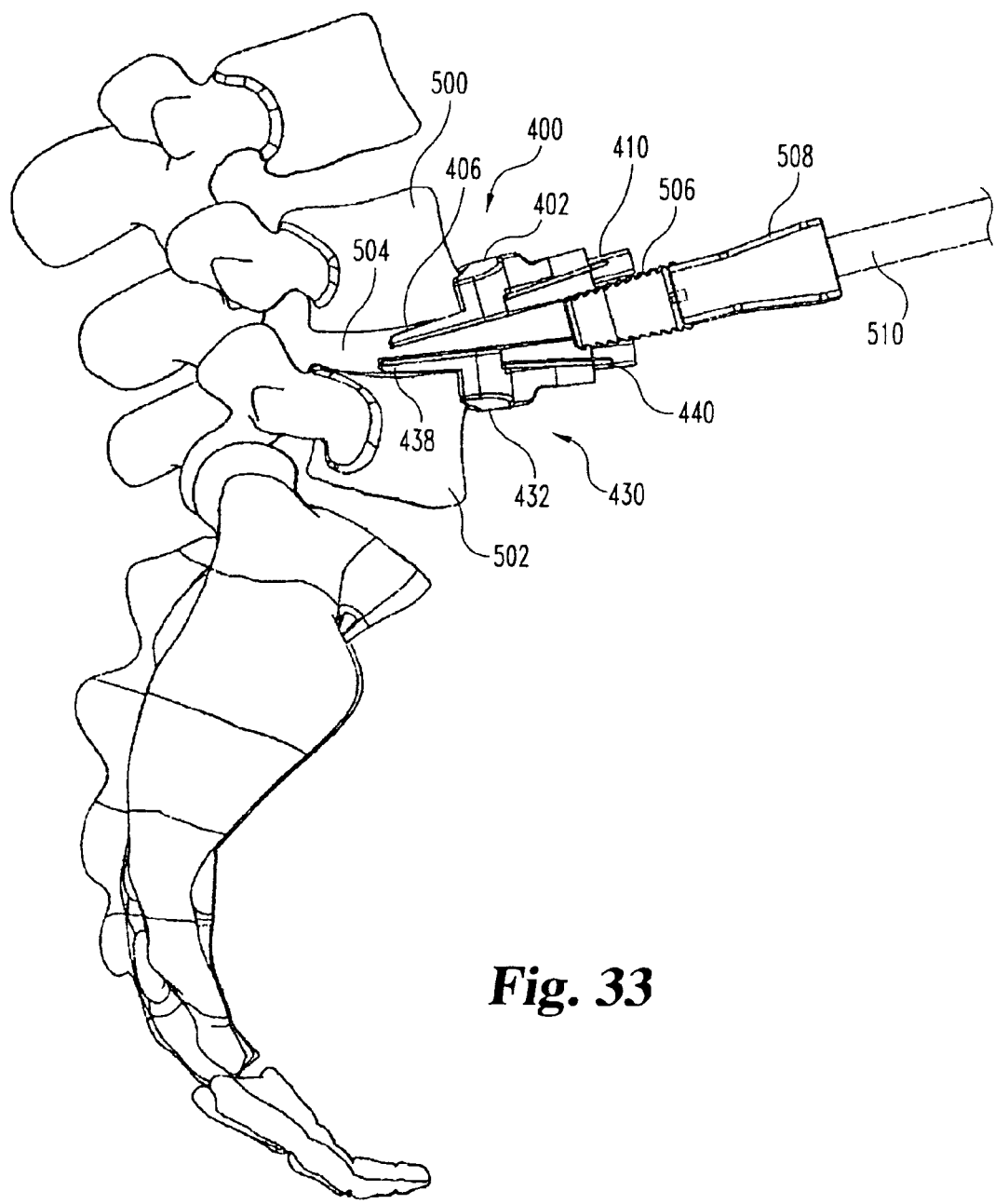
FIG. 33 is a perspective view showing insertion of a spinal implant into the disc space between the spreading members of FIG. 31.

As shown in FIG. 33, an implant 506 can be attached to a distal end 508 of an insertion instrument 510. Spreading members 400, 430 are spread apart by an actuator assembly (not shown) to provide a desired spacing between vertebrae 500, 502. Implant 506 is positioned between guide members 410, 440 and guided into disc space 504 therebetween as insertion instrument 510 is impacted or pushed forward to the desired location in disc space 504 between vertebrae 500, 502. Implant 506 can further be guided laterally between extension members 406, 408 and also the extension members of spreading member 430 to maintain the insertion path into the disc space until the implant is fully seated.

The guide members of spreading members 400, 430, 450, 480 act as a ramp to facilitate distraction of the adjacent vertebrae with insertion of the implant. The implant enters the space between the guide members at their trailing ends, and is impacted or pushed toward the distal ends to distract the vertebrae. The guide members protect the cortical bone along which the guide member extends from damage during implant insertion, and can prevent the distal extension members from subsiding into the vertebral endplates by providing a greater load bearing area during distraction. The guide members can also reduce friction during implant insertion to facilitate implant placement. It is further contemplated that the guide members can be formed with or engaged with the distal extension members and the body portion of the adjacent spreading member to provide rigidity and strength to the guide member. The low profile of the guide members and separation between the distal extension members facilitates viewing of the operative space between the spreading members.

Figure 34:
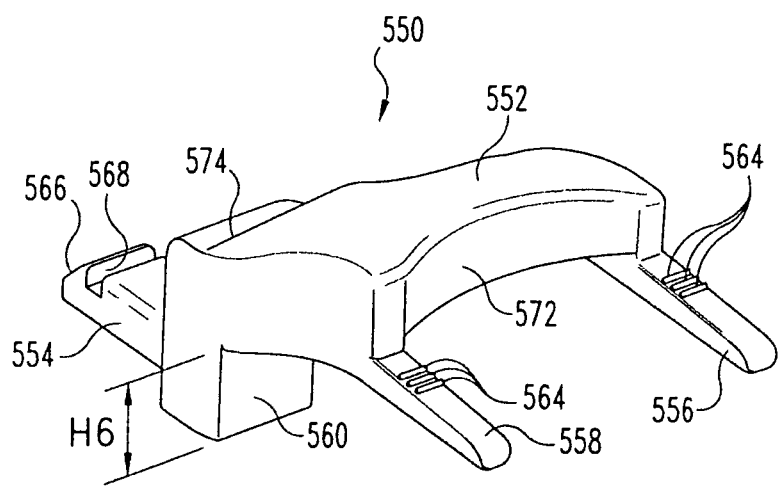
FIG. 34 is a perspective view of another embodiment spreading member.

In FIG. 34 there is shown another embodiment spreading member 550 useable with a spreader instrument, such as spreader instrument 220. Spreading member 550 can be similar to spreading member 450 discussed above, and includes a body portion 552 having distal extension members 556, 558 extending from distal end wall 572. An offset portion 574 extends between coupling portion 554 and body portion 552. Extension members 556, 558 can be provided with bone engaging features 564.

Coupling portion 554 can be provided with a tapered insertion portion 566 and a laterally extending locking member receiving portion 568. Receiving portion 568 can receive a locking member to releasably engage spreading member 550 to a spreading instrument with a locking member, such as locking members 253, 273 discussed above. The tapered insertion portion 566 moves the locking member out of alignment with the passage into which coupling portion 554 is positioned. The locking member can be spring-biased to releasably engage coupling portion 554 in receiving portion 568.

Spreading member 550 further includes a stepped region 560 that extends vertically between coupling portion 554 and body portion 552. Stepped region 560 can be provided with a height H6 between coupling portion 554 and extensions 556, 558. Stepped region 560 provides greater separation between the distal extensions members of adjacent spreading members, thus allowing greater distraction distances between vertebrae to be obtained, as may be desirable in corpectomy procedures.

Figure 35:
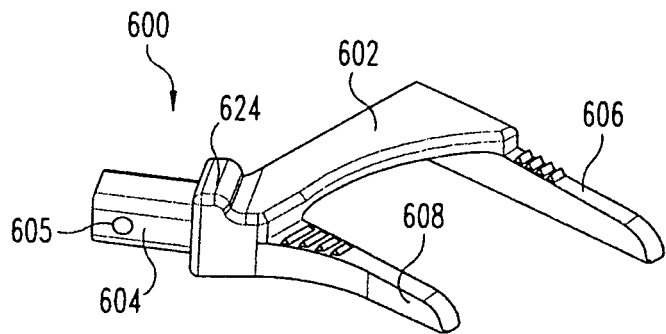
FIG. 35 is a perspective view of another embodiment spreading member.
Figure 36:
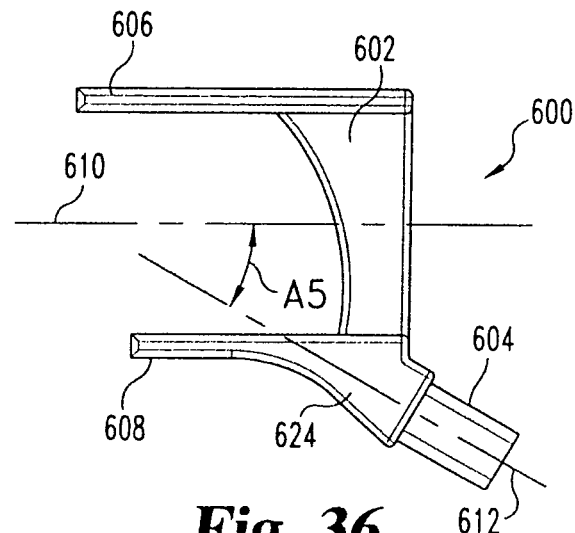
FIG. 36 is a plan view looking toward the bottom of the spreading member of FIG. 35.
Figure 37:
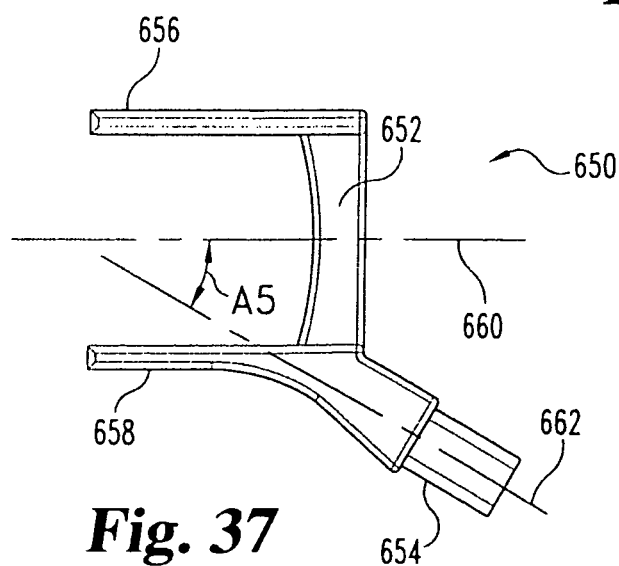
FIG. 37 is a plan view looking toward the bottom of another embodiment spreading member.

In FIGS. 35 and 36 a spreading member 600 is provided that is adapted for an anterior-oblique approach to the spinal disc space. Spreading member 600 includes a body portion 602 and a pair of extension members 606, 608 extending distally from body portion 602. An offset portion 624 extends to coupling portion 604. Coupling portion 604 includes a detent 605 for receiving a spring-loaded ball to couple spreading member 600 to an actuator assembly. Other coupling arrangements discussed herein are also contemplated.

Spreading member 600 has a central axis 610 between and extending parallel to extension members 606, 608. Offset portion 624 extends along an axis 612 oriented at angle A5 to axis 610. One embodiment contemplates that angle A5 can be in the range from 0 degrees to 90 degrees. Another embodiment contemplates that angle A5 can be in the range from 15 degrees to 60 degrees. In one specific embodiment, it is contemplated that angle A5 can be about 30 degrees.

To accommodate an anterior oblique approach, extension member 606 can be longer than extension member 608 since extension member 606 is positioned anteriorly of extension member 608 in the disc space. One embodiment contemplates that extension member 606 is about 7 millimeters longer than extension member 608. Another embodiment shown in FIG. 37 contemplates a spreading member 650 having a configuration suited for an oblique approach in which extension members 656, 658 have the same length extending from body portion 652. Spreading member 650 similarly includes a central axis 660 and an offset axis 662 extending along coupling portion 654 forming angle A5 with central axis 660. Spreading member 650 can also be inserted in an anterior-posterior orientation with at least a portion of the actuator assembly angled relative to axis 660.

Figure 38:
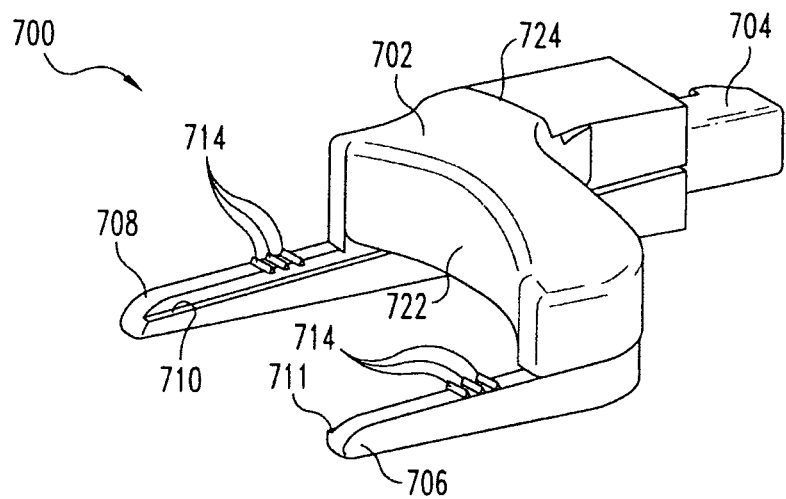
FIG. 38 is a perspective view of another embodiment spreading member.

In FIG. 38 there is shown another spreading member embodiment designated at 700. Spreading member 700 includes a body portion 702 having a distal end wall 722. First extension member 706 and second extension member 708 extend distally from and below end wall 722. Extension members 706, 708 include bone engaging features 714. An offset portion 724 extends between a coupling portion 704 and body portion 702. A support surface 710 extends along extension member 708, through body portion 702, and along offset portion 724. An opposite support surface 711 extends along extension member 706 and through body portion 702. Support surfaces are open toward the upper sides of extension members 706, 708.

Figure 39:
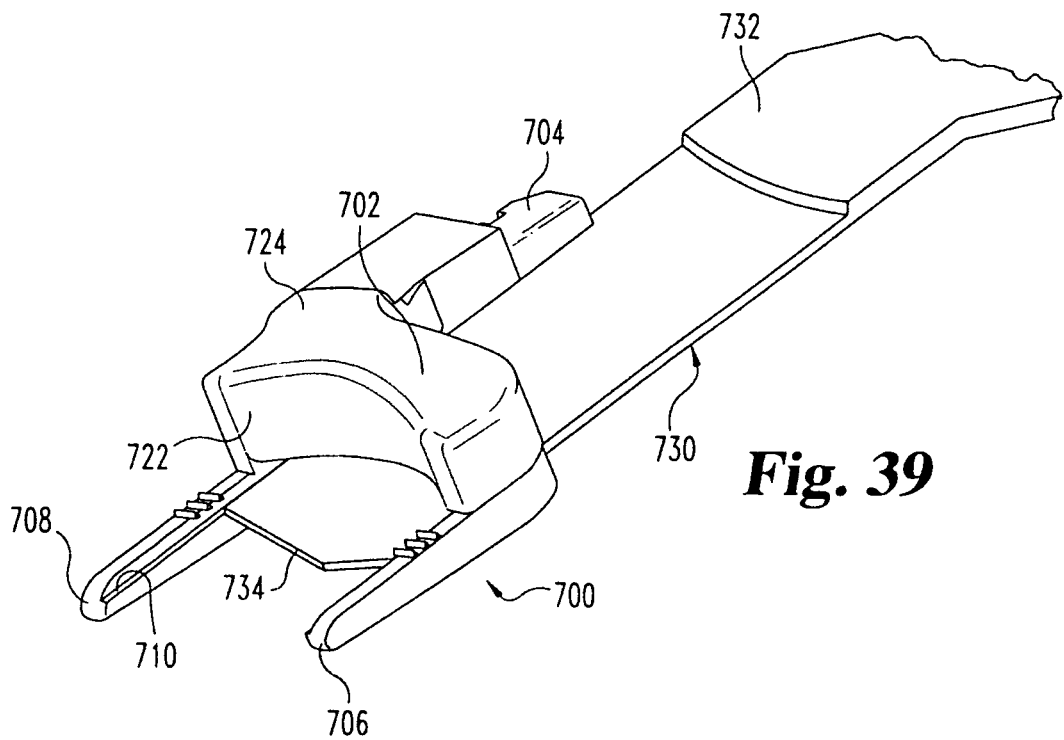
FIG. 39 is a perspective view of the spreading member of FIG. 38 guiding a cutting instrument.

As shown in FIG. 39, support surfaces 710, 711 are adapted to support at least a blade portion 734 of a cutting instrument 730, such as a chisel. Blade portion 734 extends distally from a shaft portion 732. Blade portion 734 is movable along support surfaces 710, 711 to remove, for example, bony material and/or other tissue material located between extensions 706, 708 and below support surfaces 710, 711. Extension members 706, 708 remain in contact with and support the adjacent vertebrae as cutting instrument 300 is manipulated to remove bony material between extension members 706, 708.

Figure 40:
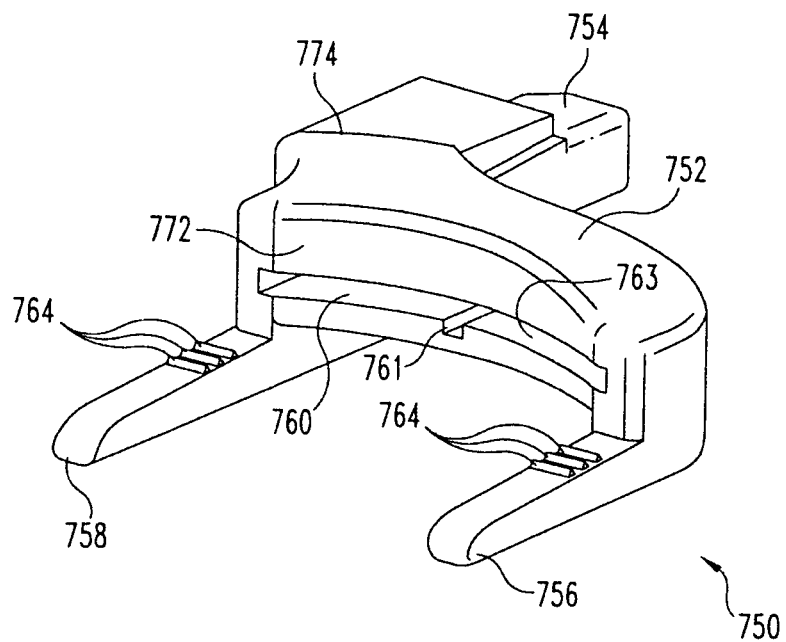
FIG. 40 is a perspective view of another embodiment spreading member.
Figure 41:
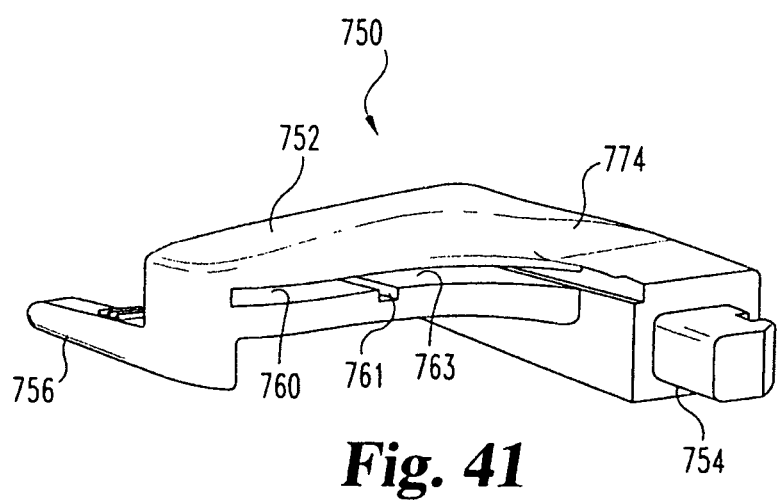
FIG. 41 is a perspective view of the spreading member of FIG. 40 looking in a direction opposite that of FIG. 40.

In FIGS. 40 and 41 there is shown another spreading member embodiment designated at 750. Spreading member 750 includes a body portion 752 having a distal end wall 772. First extension member 756 and second extension member 758 extend distally from and are offset below end wall 772. Extension members 756, 758 include bone engaging features 764 along a bone contacting surface thereof. An offset portion 774 extends between a coupling portion 754 and body portion 752. A support surface 763 is defined by a receiving slot 760 extending through body portion 752 and above extension members 756, 758. Receiving slot 760 is adapted to receive at least a blade portion of a cutting instrument, such as cutting instrument 730 discussed above. The lateral edges of receiving slot 760 are positioned between extensions members 756, 758 so that the bone material supported by extension members 756, 758 remains intact as the blade portion is moved within slot 760 to remove, for example, bony material and/or other tissue material located between extension members 756, 758 and below slot 760. The implant can then be positioned in the prepared disc space in contact with the portions of the vertebral bodies removed with the cutting instrument.

It is further contemplated that slot 760 can be provided with a groove 761 therealong. Groove 761 can receive a guide member (not shown) on the cutting instrument to maintain movement of the cutting blade within slot 760 parallel to extension members 756, 758. Groove 761 is formed in support surface 763, although other locations about slot 760 are also contemplated.

Figure 42:
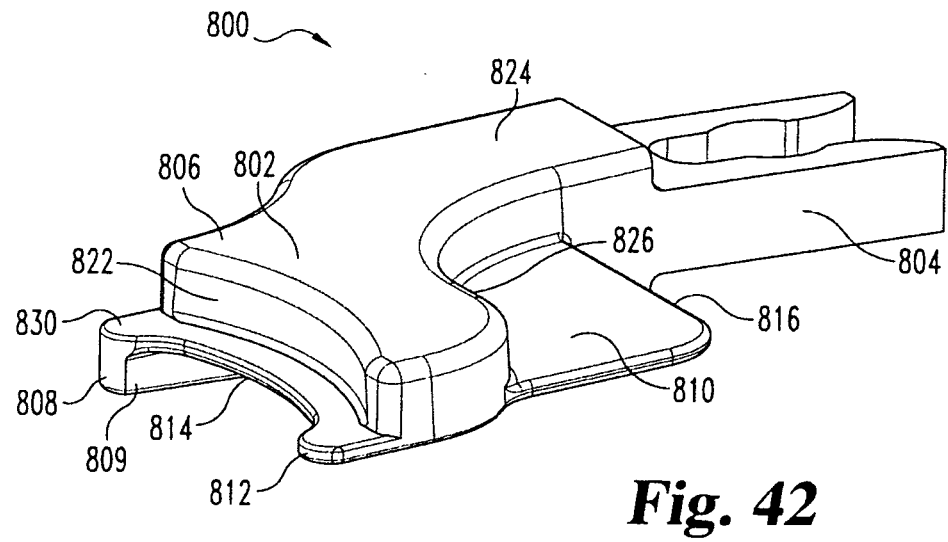
FIG. 42 is a perspective view of another embodiment spreading member.
Figure 43:
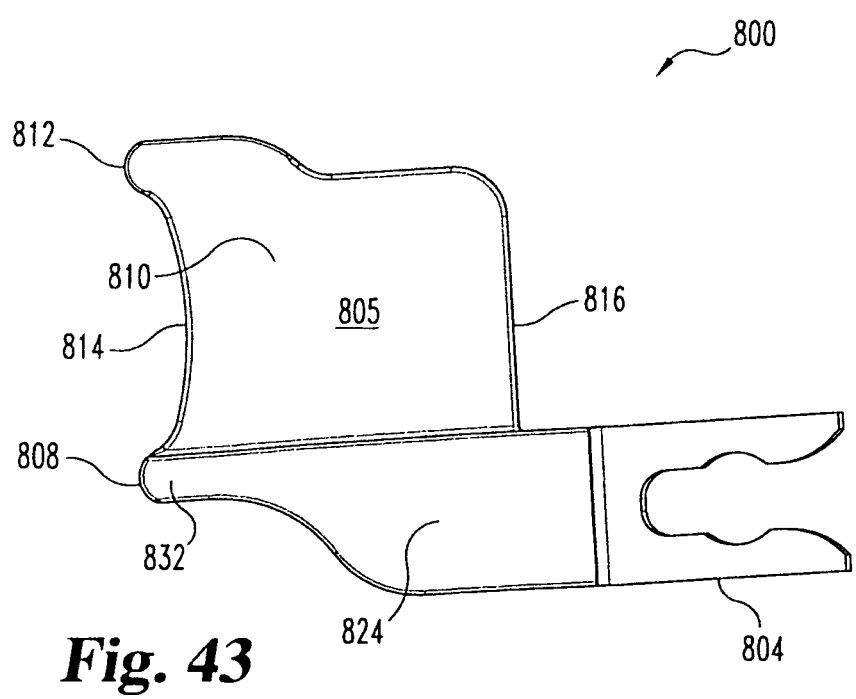
FIG. 43 is a bottom plan view of the spreading member of FIG. 42.

Referring now to FIGS. 42-43, another embodiment spreading member 800 is provided that is attachable to, for example, actuator assembly 221. Spreading member 800 includes a body portion 802 and a proximal coupling portion 804 offset from body portion 802 by offset portion 824. An extension member 808 extends distally from body portion 802 adjacent a first side thereof. Body portion 802 further includes a proximal end wall 826 and an opposite distal end wall 822 having a concave surface profile configured to reside against or along the convex curvature of an adjacent vertebral body. Body portion 802 includes an outer surface 803 and an opposite inner surface 805 oriented toward a second spreading member when assembled with the actuator assembly, it being understood that the second spreading member provides a mirror image of spreading member 800 when assembled with the actuator assembly.

Outer surface 803 and inner surface 805 are spaced from one another to provide a thickness or depth to body portion 802 that limits deflection thereof upon application of a spreading load to the adjacent bony structure. A guide member 810 extends along and forms an extension of the inner surface 805 of body portion 802 between a leading end 814 and a trailing end 816. Leading end 814 is positioned distally of body portion 802 and extends along distal end wall 822 between extension member 808 and a guide member extension 812. Guide member extension 812 is positioned adjacent a second side of body 802 opposite the first side from which extension member 808 extends. Guide member extension 812 extends distally to mimic the shape and length of extension member 808. Trailing end 816 is positioned proximally of body portion 802. In the illustrated embodiment, guide member 810 has a flat, plate-like surface profile opposite body portion 802. As discussed above, guide member 810 facilitates placement of disc space preparation instruments and implants between adjacent spreading members employing guide members 810.

Extension member 808 extends from inner surface 805 and includes a thickness between an outer surface 830 and an inner surface 832 that limits or prevents bending of extension member 808 as it applies a spreading force to the adjacent vertebra. Extension member 808 further includes a length extending from distal end wall 822 that allows outer surface 830 to contact the cortical rim of the adjacent vertebral endplate to apply a spreading force thereto. However, the length is minimized to facilitate implant insertion and/or instrument manipulation laterally of extension member 808 in the direction opposite guide member extension 812. Guide member 810 also extends distally for distal end wall 822 along the cortical rim of the adjacent vertebral endplate to facilitate passage of instruments and/or implants along the cortical rim into the disc space without engaging or catching and damaging the bony material at the cortical rim. In one specific embodiment, extension member 808 and guide member 810 extend distally about 4 millimeters from distal end wall 822. Other embodiments contemplate other lengths greater than about 2 millimeters.

Guide member extension 812 includes an inner surface that lies in the same plane as inner surface 805. This allows implants and/or instruments to be guided into the disc space between spreading members and along medial surface 809 of extension 808. The implants and/or instruments can be provided with a width extending from medial surface 809 that is greater than the width of spreading member 800 between extension member 808 and guide member extension 812. Accordingly, the implant and/or instruments are not constrained between distal extension members of spreading member 800. It is further contemplated that extension member 808 can be provided with bone engaging features, such as teeth, surface rougheneings or other surface features as discussed herein to resist movement of extension member 808 relative to the vertebral endplate.

Other forms for spreading member 800 contemplate a second extension member extending distally from body 802 along guide member extension 812. The second extension member can be provided with a relatively short length to allow instruments and implants to be positioned distally thereof when the second extension member is in the disc space.

The instruments discussed herein can be provided as a kit including an actuator assembly and various pairs of spreading members removably attachable to the actuator assembly and from which the surgeon can select depending on the procedure. For example, the kit can include an actuator assembly and any one or combination of a set of single extension spreading members such as shown in FIG. 6; one or more sets of double extension spreading members forming various angles between guide members such as shown in FIGS. 29 and 30; one or more sets of spreading members without guide members and/or for various approaches to the disc space such as shown in FIGS. 34-37; one or more sets of spreading members with an offset region such as shown in FIG. 34; one or more sets of spreading members adapted to guide a cutting instrument, such as shown in FIGS. 39 and 40; and one or more sets of spreading members with a single extension and guide member, such as shown in FIGS. 42-43.

While the invention has been illustrated and described in detail in the drawings and foregoing description, the same is to be considered as illustrative and not restrictive in character, and that all changes and modifications that come within the spirit of the invention are desired to be protected.

What is claimed is:

1. An instrument for separating bony structures, comprising:
   an actuator assembly comprising a first handle and a second handle;
   a spreader assembly at a distal end of said actuator assembly, wherein said spreader assembly includes first and second spreading members positionable between the bony structures and movable away from and toward one another with said actuator assembly, wherein said first and second spreading members each include:
   a coupling portion extending from and removably engaged to said actuator assembly;
   a body portion extending from said coupling portion;
   a first extension member extending distally from a first side of said body portion, said first extension member including a bone contacting surface therealong for engaging the bony structure positioned thereagainst; and
   a second extension member spaced from said first extension member and extending distally from a second side of said body portion, said second extension member including a bone contacting surface therealong for engaging the bony structure positioned thereagainst; and
   a linkage assembly comprising a first link member pivotally coupled to the first and second handles and a second link member pivotally coupled to the first and second handles, the first and second link members being pivotally coupled to one another,
   wherein at least one of said first and second spreading members includes a stepped region extending vertically from said coupling portion to said body portion, said stepped region vertically spacing said body portion and said first and second extension members of said at least one of said first and second spreading members from said body portion and said first and second extension members of the other of said first and second spreading members when said actuator assembly is in an unactuated position to place said spreading members at a minimum height relative to one another.

2. The instrument of claim 1, wherein said bone contacting surfaces each include a convex curvature therealong and a number of grooves in said convexly curved portion forming said bone engagement features.

3. The instrument of claim 1, wherein said body portion of each of said first and second spreading members includes an outer surface, an inner surface oriented opposite said bone contacting surfaces of said first and second extension members, and a distal end wall concavely curved between said first and second extension members.

4. The instrument of claim 3, wherein said first and second extension members of each of said first and second spreading members extend from said distal end wall adjacent said inner surface.

5. The instrument of claim 1, wherein for each of said first and second spreading members said first extension member extends distally further than said second extension member.

6. The instrument of claim 1, wherein said body portion of each of said first and second spreading members includes an outer surface, an inner surface oriented opposite said bone contacting surfaces of said extension members, a distal end wall, and a proximal end wall, said body portion further comprising a slot extending between said proximal and distal end walls sized to receive a cutting instrument therethrough.

7. The instrument of claim 6, wherein said slot is sized to guide the cutting instrument between said bone contacting surfaces of said first and second extension members.

8. The instrument of claim 7, wherein said body portion includes a groove in communication with said slot to maintain alignment of the cutting instrument.

9. The instrument of claim 1, wherein said body portion of each of said first and second spreading members includes an outer surface, an inner surface oriented opposite said bone contacting surfaces of said first and second extension members, a distal end wall, and a proximal end wall, said body portion further comprising a support surface extending along said inner surface and each of said first and second extension members to support a cutting instrument therealong.

10. An instrument for separating bony structures, comprising:
   an actuator assembly comprising a first handle and a second handle;
   a spreader assembly at a distal end of said actuator assembly, wherein said spreader assembly includes first and second spreading members movable away from and toward one another with said actuator assembly, said spreading members each including a body portion and a pair of extension members extending distally from said body portion, said spreading members further each including a support surface extending from a proximal end of said body portion through a distal end of said body portion and on each of said pair of extensions for guiding a cutting instrument between said pair of extension members, wherein said support surfaces of said first and second spreading members face away from one another in opposite directions; and
   a linkage assembly comprising a first link member coupled to the first and second handles and a second link member coupled to the first and second handles, the first and second link members being pivotally coupled to one another.

11. The instrument of claim 10, wherein said body portion of each of said first and second spreading members includes an outer surface, an inner surface oriented toward the inner surface of the other body portion, a distal end wall, and a proximal end wall, said body portion further comprising a slot defining a portion of said support surface, said slot extending between and opening at said proximal and distal end walls.

12. The instrument of claim 10, wherein said body portion of each of said first and second spreading members includes an outer surface, an inner surface oriented toward the inner surface of the other body portion, a distal end wall, and a proximal end wall, said support surface extending along said inner surface of said body portion and along each of said first and second extension members.

13. The instrument of claim 10, wherein said body portion of at least one of said first and second spreading members includes a stepped region extending from said actuator assembly, said stepped region spacing said first and second extension members of said at least one of said first and second spreading members from said first and second extension members of the other of said first and second spreading members with said actuator assembly in an unactuated position.

14. The instrument of claim 10, wherein each one of said pair of extension members of each of said spreading members includes a number of teeth extending from a bone contacting surface thereof.

15. The instrument of claim 10, further comprising an adjustment mechanism coupled to said actuator assembly.

16. An instrument for separating adjacent vertebrae, comprising:
   an actuator assembly comprising a first handle and a second handle;
   a spreader assembly at a distal end of said actuator assembly, wherein said spreader assembly includes first and second spreading members positionable between the adjacent vertebrae and movable away from and toward one another with said actuator assembly, said spreading members each including a body portion and first and second extension members spaced from one another and extending distally from said body portion, said first extension member including a length that is greater than a length of said second extension member; and
   a linkage assembly comprising a first link member coupled to the first and second handles and a second link member coupled to the first and second handles, the first and second link members being pivotally coupled to one another.

17. The instrument of claim 16, wherein said first and second extension members are adapted for each of said body portions to be positioned along an anterior-oblique aspect of the adjacent vertebrae.

18. The instrument of claim 16, wherein said first and second extension members of each of said spreading members each include a number of teeth extending from a bone contacting surface thereof.

19. The instrument of claim 16, wherein said body portion of each of said first and second spreading members includes an outer surface, an inner surface oriented toward the inner surface of the other body portion, a distal end wall, and a proximal end wall, each of said body portion further defining a support surface extending along said inner surface of said body portion and along each of said first and extensions of said body portion, said support surfaces facing away from one another in opposite directions and each is configured to support and guide a cutting instrument along said inner surface of said respective body portion and along said first and second extensions extending from said respective body portion.

20. The instrument of claim 16, wherein said body portion of at least one of said first and second spreading members includes a stepped region extending from said actuator assembly, said stepped region spacing said first and second extension members of said at least one of said first and second spreading members from said first and second extension members of the other of said first and second spreading members with said actuator assembly in an unactuated position to provide a minimum vertical spacing between said extensions of said body portions.

* * * * *